US006415181B1

United States Patent
Schu et al.

(10) Patent No.: US 6,415,181 B1
(45) Date of Patent: Jul. 2, 2002

(54) IMPLANTABLE MEDICAL DEVICE INCORPORATING ADIABATIC CLOCK-POWERED LOGIC

(75) Inventors: Carl A. Schu, Plymouth; Daniel R. Greeninger, Coon Rapids; David L. Thompson, Fridley, all of MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/513,045

(22) Filed: Feb. 25, 2000

(51) Int. Cl.[7] .............................................. A61N 1/362
(52) U.S. Cl. ..................................................... 607/16
(58) Field of Search ............................... 607/1, 2, 9, 8, 607/4, 5, 16

(56) References Cited

U.S. PATENT DOCUMENTS

| | | | |
|---|---|---|---|
| 4,515,159 A | * 5/1985 | McDonald et al. ............ | 607/9 |
| 5,014,057 A | 5/1991 | Mintzer | |
| 5,305,463 A | 4/1994 | Fant et al. | |
| 5,473,269 A | 12/1995 | Dickinson | |
| 5,473,526 A | 12/1995 | Svensson et al. | |
| 5,506,520 A | 4/1996 | Frank et al. | |
| 5,559,478 A | 9/1996 | Athas et al. | |
| 5,655,090 A | 8/1997 | Weingart | |
| 5,676,686 A | * 10/1997 | Jensen et al. .................. | 607/9 |
| 5,822,609 A | 10/1998 | Richter | |
| 5,986,466 A | 11/1999 | Sobelman et al. | |
| 5,986,476 A | 11/1999 | De | |
| 5,999,849 A | 12/1999 | Gore et al. | |
| 6,029,087 A | * 2/2000 | Wohlgemuth .................. | 607/9 |

OTHER PUBLICATIONS

Gail Robinson, "New design approach recycles electrons to save power—Clock powered circuits set efficiency record", Electronic Engineering Times, 1997, n. 983, PG. 37.*

"Clockless Logic Overview," @ http://www.sanders.com/hpc/CL/Overview.html.

37 A Fully Asynchronous Digital Signal Processor Using Self–Timed Circuits, *IEEE Journal of Solid–State Circuits*, vol. 25, No. 6, 12/90, pp. 1526–1536.

Fant et al. in "NULL Convention Logic™" (Theseus Logic, Inc., 1997, 35 pp.).

Wang et al. in "Technology Independent Design Using NULL Convention Logic™" (Theseus Logic, inc., Oct. 19, 1998 19 pp.).

Cogency Technology, @ http//:www.cogency.co.uk/tech/index.html, © 1999, 8 pp.

Svensson et al.,"Driving a capacitive load without dissipating $fCV^2$," 1994 IEEE, Proc of the International Symposium of Low–Power Electronics and Design, San Diego, CA, Oct. 10–12, 1994.

(List continued on next page.)

*Primary Examiner*—George R. Evanisko
(74) *Attorney, Agent, or Firm*—Girma Wolde-Michael

(57) ABSTRACT

Improved operating system architecture for an implantable medical device incorporating adiabatic clock-powered logic alone or in conjunction with conventional clocked logic or self-timed logic for reducing power consumption and increasing and improving processing capabilities is disclosed. The adiabatic clock-powered logic is employed to implement digital signal processors (DSPs) including analog to digital (ADC) signal converters, a state machine or the components of microprocessor cores, e.g., the CPU, arithmetic logic units (ALU), on-chip RAM and ROM and data and control buses, and other logic units, e.g., additional RAM and ROM, a direct memory address (DMA) controller, a block mover/reader, a cyclic redundancy code (CRC) calculator, and certain uplink and downlink telemetry signal processing stages. The adiabatic clocked CMOS logic is incorporated into the same IC or ICs with clocked CMOS logic and provides manufacturing economies.

31 Claims, 12 Drawing Sheets

OTHER PUBLICATIONS

Gail Robinson, "New design approach recycles electrons to save power—Clock–powered circuits set efficiency record," Electronic Engineering Times, 1997, n 983, PG37.

Athas et al., "Energy–Recovery CMOS for Highly Pipelined DSP Designs," USC/Information Sciences Institute; IEEE, Proc. of the International Symposium on Low–Power electronics and Design, Monterey, CA, Aug. 12–14, 1996.

Chandrakasan et al., "Low–Power Digital CMOS Design," Kluwer Academic Publishers, 1995, Third Printing 1998.

Athas et al., "Low–Power Digital Systems Based on Adiabatic–Switching Principles," IEEE Trasactions of VLSI Systems, pp. 398–407, Dec. 1994.

Athas et al., "An Energy–Efficient CMOS Line Driver Using Adiabatic Switching," IEEE, Proc. Of the Fourth Great Lakes Symposium on VLSI Design, pp 159–164, Mar. 1994.

Lars Svensson, "AC–1: A Clock–Powered Microprocessor," Enterprise Integration Systems Division, USC/Information Sciences Institute, Aug. 20, 1997.

Tzartzanis et al., "Clock–Powered Logic for a 50 MHz Low–Power RISC Datapath," Information Sciences Institute, The Univ. of Southern California, Feb. 8, 1997.

Tzartzanis et al., "Retractile Clock–Powered Logic," Information Sciences Institute, Univ. of Southern California, Aug. 16, 1999.

Tzartzanis et al., "Clock–Powered CMOS: A Hybrid Adiabatic Logic Style for Energy–Efficient Computing," Information Sciences Institute, Univ. of Southern California, Mar. 22, 1999.

Athas et al., "AC–1: A Clock–Powered Microprocessor," 1997 IEEE, Proc. Of the International Symposium on Low–Power Electronics and Design, Monterey, CA, Aug. 18–20, 1997.

Tzartzanis et al., "Clock–Powered Logic for a 50 MHz Low–Power RISC Datapath," 1997 IEEE, Digest of Technical Paperes of the International Solid–State Circuits Conference, San Francisco, CA Feb. 6–8, 1997.

* cited by examiner

_US 6,415,181 B1_

IMPLANTABLE MEDICAL DEVICE INCORPORATING ADIABATIC CLOCK-POWERED LOGIC

REFERENCE TO RELATED APPLICATION

Reference is hereby made to commonly assigned U.S. patent application Ser. No. (P-9201.00) filed on even date herewith for IMPLANTABLE MEDICAL DEVICE INCORPORATING SELF-TIMED LOGIC and to U.S. patent application Ser. No. 09/467,288 filed on Dec. 20, 1999, for POWER DISSIPATION REDUCTION IN MEDICAL DEVICES USING ADIABATIC LOGIC.

FIELD OF THE INVENTION

This invention relates generally to implantable medical devices, and more particularly to an improved operating system architecture incorporating adiabatic clock-powered logic, alone, or in conjunction with self-timed logic, for reducing power consumption and increasing and improving processing capabilities.

BACKGROUND OF THE INVENTION

A wide variety of implantable medical devices (IMDs) that employ electronic circuitry for providing electrical stimulation of body tissue and/or monitoring a physiologic condition are known in the art. A number of IMDs of various types are known in the art for delivering electrical stimulating pulses to selected body tissue and typically comprise an implantable pulse generator (IPG) for generating the stimulating pulses under prescribed conditions and at least one lead bearing a stimulation electrode for delivering the stimulating pulses to the selected tissue. For example, cardiac pacemakers and implantable cardioverter/defibrillators (ICDs) have been developed for maintaining a desired heart rate during episodes of bradycardia or for applying cardioversion or defibrillation therapies to the heart upon detection of malignant tachyarrhythmias. Other IMDs have been developed for applying electrical stimulation or other therapies, e.g., drugs, to nerves, the brain, muscle groups and other organs and body tissues for treating a variety of conditions.

Over the past 40 years, such IMDs have evolved from relatively bulky, crude, and short-lived devices providing simple stimulation therapies and monitoring functions to complex, long-lived, and miniaturized IMDs, e.g., cardiac IMDs providing a wide variety of pacing and/or cardioversion and defibrillation therapies and/or monitoring functions. Numerous other programmable functions have been incorporated including enhanced capacity to detect and discriminate cardiac arrhythmias, to store data and to uplink telemetry data related to arrhythmia episodes and applied therapies (if any). Moreover, the capability of interrogating stored device data and initiating real time uplink telemetry of physiologic data, e.g. the real time cardiac EGM and blood pressure and the like, have been incorporated into such IMDs.

The earliest implantable pacemaker IPGs employed very simple analog circuit oscillators formed by discrete transistors and other circuit components and were very short-lived and electrically inefficient. Integrated circuit (IC) technology and battery improvements were made that enabled hermetic sealing of IMD housings, improved reliability and lengthened the operating life of the IMD. The MEDTRONIC® SPECTRAX® pacemaker IPGs incorporated an analog IC with digital IC into a digital clocked logic operating system architecture providing an array of sophisticated operating functions, programmability of operating modes and parameters, data storage, and uplink telemetry functions. Successive generations of IMDs of this type have incorporated increased operating modes and functions through further improvements in circuitry and long-lived, low current output, low voltage batteries. Most recently, a wide number of IMD system architectures have been developed that incorporate custom microcomputers comprising a microprocessor, RAM and ROM, bus, and related elements of a typical microcomputer and other control logic, memory, input signal processing circuitry and therapy delivery output circuitry. The complexity of the circuitry, the functions provided, the longevity, and the reliability of the IMDs have all increased dramatically while the IMD size has decreased.

Current IMD operating system architectures typically are embodied in two or more ICs and discrete components mounted to one (or more) substrate employing hybrid fabrication circuitry techniques. Certain of the ICs or circuitry on a particular IC perform analog functions, input signal processing, and output therapy delivery. Digital logic ICs or circuitry are formed employing complementary metal oxide semiconductor (CMOS) fabrication technology. The digital logic ICs perform signal processing, timing, and state change functions embodying Boolean logic timed synchronously by a system-wide, clock, and are referred to herein as "clocked logic" ICs or circuits.

The power consumption of CMOS circuits consists generally of two power consumption factors, namely "dynamic" power consumption and "static" power consumption. The static power consumption is only due to current leakage, as the quiescent current of such circuits is zero. Dynamic power consumption is due to the current required to charge internal and load capacitances during switching, i.e., the charging and discharging of such capacitances, and is the dominant form of power consumption for CMOS technology. The dynamic power (P) for the CMOS circuit is a function of nodal capacitance (C), the clock or switching frequency (F), and the supply voltage ($V_{DD}$) in accordance with the formula $P = C V_{DD}^2 F$.

By way of explanation, reference is made FIG. 1, which shows a simple CMOS buffer circuit 10 operated using a dual rail clock ø to provide a logic level output at node 22 that is inverse to the applied input. A logic level input signal is provided to the gate terminals of a P-channel MOS (pMOS) FET 14 and N-channel MOS (nMOS) FET 16, the dual rail clocks are is applied to the gate terminals of a pMOS FET 12 and nMOS FET 18. Load capacitor 20 is coupled between the node 22 at the source and drain terminals of the pMOS and nMOS FETs 18 and 12. As will be appreciated, the pMOS FET 14 is biased to switch ON and the nMOS FET 16 is biased to switch OFF when the input is driven LOW, and, conversely, the pMOS FET 14 is biased to switch OFF and the nMOS FET 16 is biased to switch ON when the input is driven HIGH. The nMOS FET 12 is biased to switch ON by the clock ø applied to its gate, and the pMOS FET 18 is biased to switch ON by the inverted clock ø applied to its gate.

The pMOS FET 14 and pMOS FET 18 both switch ON only when the input is driven LOW and when the inverted clock ø occurs. The capacitor 20 is then charged from the voltage source $V_{DD}$, and a logical one (HIGH) is registered at the output (node 22).

Similarly, the nMOS FET 16 and nMOS FET 12 both switch on only when the input is driven LOW and when the clock ø occurs. The charge stored in the capacitor 20 is then discharged through the nMOS FETs 16 and 12 ground, whereby a logical zero (LOW) is registered at node 22.

Each transition of the input signal to LOW during the inverted clock ø thereby results in the transfer of a certain amount of energy from the battery supplying $V_{DD}$ to capacitor 20, and that energy is then simply dissipated when the input signal switches HIGH and the clock ø occurs. In addition, the clock energy is itself dissipated during each clock cycle. Thus, in conventional CMOS switches, such as those shown in FIG. 1, each transfer of charge is coupled with the dissipation of a certain amount of power (P) in accordance with the above formula.

Efforts have been made conventionally in CMOS IC designs used in IMDs to scale down the supply voltage for an entire device (e.g., a hybrid or IC) to provide the minimally required power to reliably operate all of the clocked logic of the device. For example, in the Medtronic SYMBIOS® pacemaker IPGs, the logic circuitry was powered by a voltage regulator controlling the IC supply voltage to a "sum of thresholds" supply. This regulator provided a supply to the IC (i.e., $V_{DD}$) of several hundred millivolts above the sum of the n-channel and p-channel thresholds of the CMOS transistors making up the IC. This regulator was self calibrating regarding manufacturing variations of the transistor thresholds. This same approach of specifying a high enough voltage to account for fabrication variances is followed even when only a single such CMOS IC is employed in the IMD system. Therefore, in practice, excessive power may be consumed by the CMOS IC or ICs of the IMD operating system.

Other IMDs have reduced power consumption in other varied manners, e.g., by shutting down analog blocks and/or shutting off clocks to logic blocks not being used at particular times. In commonly assigned U.S. Pat. No. 5,916,237, it is proposed that the power delivered to selected sections of the digital logic circuitry in IMDs be cycled between power ON and power OFF states to reduce static power consumption. In many applications, most of the digital logic circuitry may be turned off at various times during each system clock cycle, which reduces static power consumption and average power consumption of the is digital clocked logic circuitry.

In addition, microprocessor based IMDs provided by virtually all pacemaker and ICD manufacturers have historically used a "burst clock" design to perform processing operations at a relatively high clock rate (e.g., generally 500–1000 KHz) for relatively short periods of time to gain the benefit of a "duty cycle" to reduce average current drain. A much lower frequency clock (e.g., generally 32 KHz) is used for other timing and control circuitry and/or the processor when not in the high clock rate, burst clock mode. A few illustrative examples which describe the use of a burst clock are provided in U.S. Pat. Nos. 4,561,442, 5,022,395, 5,154,170, and 5,388,578.

These approaches to reducing the dynamic power dissipation can be summarized as reducing the operating voltage $V_{DD}$ to the lowest level ensuring reliable operation, reducing the capacitance C, and reducing the number of switching operations which occur within an IC over a set time period. Even with these improvements, clocked logic CMOS circuits assembled from logic gates, flip-flops, and other Boolean logic blocks used in IMD system architectures suffer from several limitations and disadvantages.

Recently, the concept of using adiabatic logic has been proposed as a method of reducing energy dissipation in IMDs. Simply stated, adiabatic logic, sometimes referred to as "resonant", clock-powered" or "step-wise charging clocked logic" seeks to avoid or minimize any energy exchange with the environment, that is dissipation of energy as heat.

A discussion of adiabatic logic principles and alternative circuit implementations appears in chapter 6, entitled "Adiabatic Switching" by L. Svennson, appearing in the book entitled *LOW POWER DIGITAL CMOS DESIGN* edited by A. P. Chandrakasan and R. W. Broderson (Kluwer Academic Publishers, 1995) for example. The suggestion of using such circuits in IMDs, e.g., cardiac pacemakers, has been made (see "New Design Approach Recycles Electrons to Save Power—Clock-powered Circuits set Efficiency Record" appearing in *Electronic Engineering Times*, 1997, no. 983, page 37), although no implementation has yet appeared.

Adiabatic clock-powered logic requires the use of specialized single phase or multiple phase clocks. When using any sort of clocked logic, it is necessary to route clock distribution over the complete IC chip area as a clock tree of discrete electrical conductors or lines to reach all clocked logic. The clock tree takes up IC chip real estate that could be used to increase device functions or memory capacity, dissipates power as heat, and increases overall power drain of the IC, decreasing useful life of the IMD battery. Complex timing analysis and worst case design analysis and simulation are required in clocked logic circuits to ensure design integrity because of possible clock skew and the resultant timing errors induced by race conditions. Consequently, it would be desirable to minimize the use of IC real estate occupied by the clock tree, to simplify design analysis and simulation of the IMD system architecture, and to decrease power consumption.

For a time, early, large scale and relatively primitive, general purpose computers did not rely upon clocked logic or CMOS circuitry, and instead operated asynchronously. However, clocked computer system architectures replaced the early asynchronous architectures, and computer clock speeds have steadily increased. Increasing the speed at which a digital logic device transitions between logic states, commonly referred to as switching speed, has long been a primary motivation behind many advancements in the semiconductor arts to increase computing and signal processing power. Increasing the switching speed of a clocked logic circuit, however, results in a proportional increase of the dynamic power (P) consumed by the circuitry as it switches more frequently between logic states as described above. The dynamic power (P) is dissipated as heat in high clock rate microprocessors employed in personal computers, necessitating cooling fans and large scale heat sinks to avoid destructive heat buildup.

In recent years, a variety of self-timed or asynchronous logic schemes have been devised in the effort to reduce the reliance upon high speed clocks in very high speed clocked logic circuits used in computing and telecommunications devices. Self-timed or asynchronous logic systems have therefore been proposed to eliminate or minimized clock trees in such high speed ICs for these applications.

Computing power requirements in IMDs have also increased dramatically in recent years while circuitry, batteries and other components have been decreased in size to achieve small sized, long-lived IMDs favored by physicians and patients. It is desirable to continue to reduce size and power consumption and increase and improve processing capabilities of such IMDs.

SUMMARY OF THE INVENTION

In accordance with one aspect of the present invention, an IMD system architecture implemented in clocked logic employs adiabatic clock-powered logic to minimize power dissipation for certain functions. For example, certain functions of IMDs require precise timing out of time periods that are measured in terms of milliseconds to hours, days or weeks or precise timing of encoded data signals that are employed in uplink telemetry from the IMD to an external programmer. Such time periods are timed out as multiples of a stable system clock. Adiabatic clock-powered logic is optimal for timing out such time periods and providing time-dependent encoding of RF signal pulses in uplink telemetry signals. Other circuitry of IMDs may also be implemented advantageously using adiabatic clock-powered CMOS logic.

In accordance with a further aspect the present invention, self-timed logic, alternatively called clockless logic or asynchronous logic, is incorporated into the same IC or ICs with adiabatic clocked CMOS logic, and is used in lieu of clocked logic for certain circuits of an IMD system architecture. Preferably, the self-timed logic implements digital signal processors (DSPs) including analog to digital (ADC) signal converters, a state machine or the components of microprocessor cores, e.g., the CPU, arithmetic logic units (ALU), on-chip RAM and ROM and data and control buses, and other logic units, e.g., additional RAM and ROM, a direct memory address (DMA) controller, a block mover/reader, a cyclic redundancy code (CRC) calculator, and certain uplink and downlink telemetry signal processing stages.

The self-timed CMOS logic can be incorporated into the same IC or ICs with adiabatic clocked CMOS logic in a manner that minimizes the size of the clock tree serving the clocked CMOS logic allows for efficient allocation of chip real estate, and provides manufacturing economies.

The use of self-timed logic with adiabatic clock-powered logic in IMD ICs advantageously reduces dynamic power consumption and dissipation in the remaining clock tree. The diminution of the clock tree makes IC chip real estate available to incorporate further clocked and self-timed logic therein to increase RAM or to add further IMD functional operations. The decrease in dynamic power consumption and the available real estate enables the addition of further features to the IMD operating system while maintaining a desired battery lifetime. The use of self-timed logic circuits reduces complex timing analysis and worst case design analysis and simulation significantly. The adiabatic operation of the adiabatic clock-powered logic reduces its energy consumption, whereby energy consumption of the entire CMOS logic of the IMD is reduced from energy consumed by conventional clocked logic.

BRIEF DESCRIPTION OF THE DRAWINGS

These and other advantages and features of the present invention will be appreciated as the same becomes better understood by reference to the following detailed description of the preferred embodiment of the invention when considered in connection with the accompanying drawings, in which like numbered reference numbers designate like parts throughout the figures thereof, and wherein.

DETAILED DESCRIPTION OF THE PREFERRED EMBODIMENTS OF THE INVENTION

In a first aspect of the present invention, the preferred embodiments of the disclose uses of adiabatic clock-powered logic circuits where it is possible and desirable to do so in IMD system architectures. Generally speaking, in accordance with the present invention, functions that depend upon precise time-out of fixed or variable time periods are implemented using adiabatic clock-powered logic. Two phase clock signals are generated by a system clock that may itself be implemented in adiabatic clock-powered logic. Generally, time-dependent functions performed by IMDs involve time periods in the range between 0.1 milliseconds to hours, days or weeks, and a relatively low basic clock speed is used for such timing in the present invention using clock driven timers. The remaining circuits of the system architecture may also be implemented in adiabatic clock-powered logic.

In a second aspect of the present invention, the preferred embodiments of the present invention disclose uses of adiabatic clock-powered logic and self-timed logic circuits in preference to clocked logic circuits where it is possible and desirable to do so in IMD system architectures. Generally speaking, in accordance with this aspect of the present invention, functions that depend upon precise time-out of fixed or variable time periods are implemented using adiabatic clock-powered logic, and functions that are not critically time-dependent, such as computations performed by the microcomputer based control system, are implemented in self-timed logic.

Figure 2:
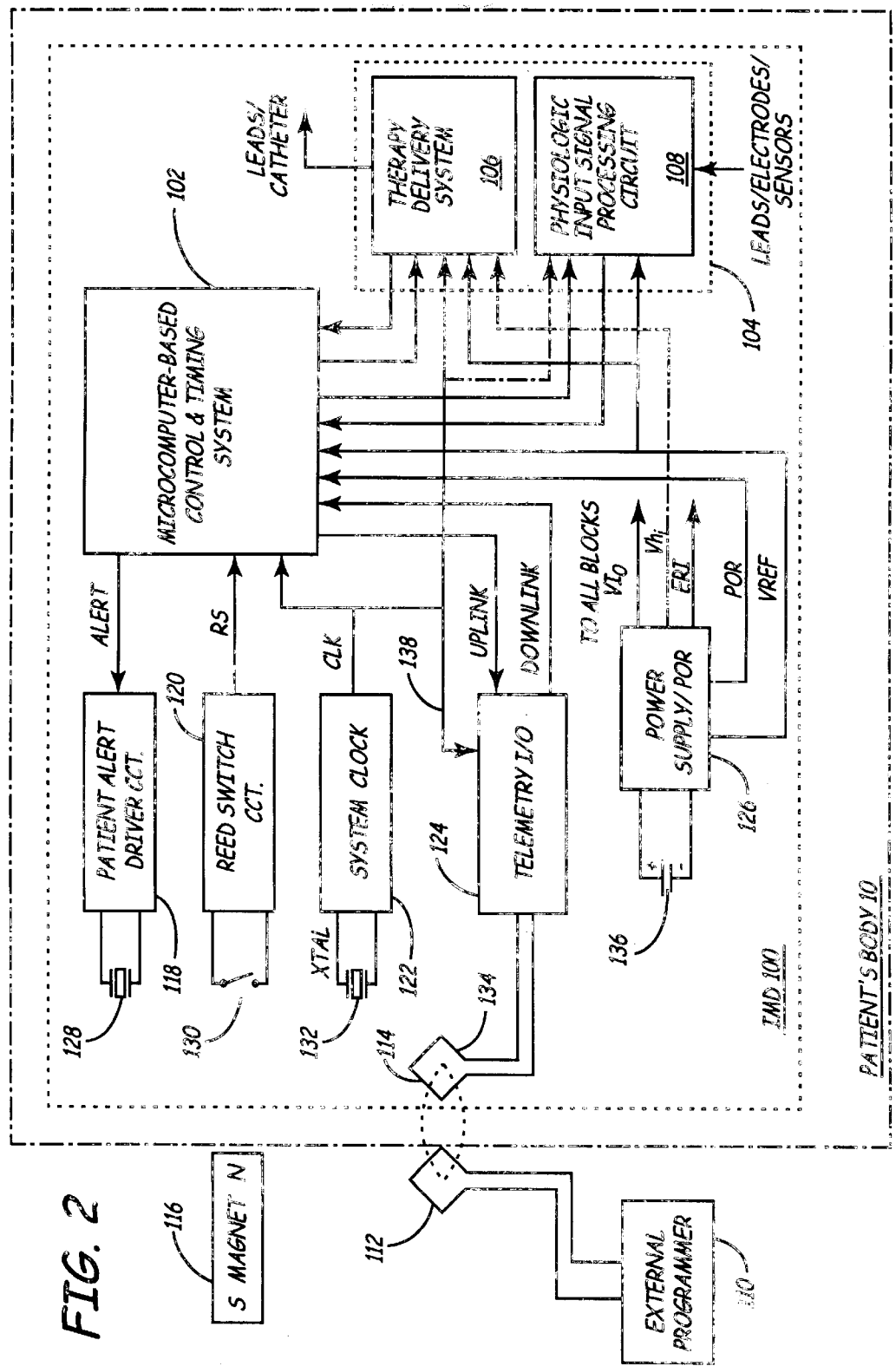
FIG. 2 is a block diagram of a system architecture of an exemplary IMD that incorporates delivery of a therapy and/or physiologic input signal processing in which adiabatic clock-powered logic can be employed alone or in conjunction with self-timed logic in accordance with the present invention.

FIG. 2 depicts a system architecture of an exemplary IMD 100 implanted into a patient's body 10 that provides delivery of a therapy and/or physiologic input signal processing in which self-timed logic and/or adiabatic clock-powered logic are incorporated in accordance with the present invention. The typical IMD 100 has a system architecture that is constructed about a microcomputer-based control and timing system 102 which varies in sophistication and complexity depending upon the type and functional features incorporated therein. The functions of microcomputer-based IMD control and timing system 102 are controlled by firmware and programmed software algorithms stored in RAM and ROM including PROM and EEPROM and are carried out using a CPU, ALU, etc., of a typical microprocessor core architecture. The microcomputer-based IMD control and timing system 102 may also include a watchdog circuit, a DMA controller, a block mover/reader, a CRC calculator, and other specific logic circuitry coupled together by on-chip data bus, address bus, power, clock, and control signal lines in paths or trees in a manner well known in the art. In accordance with the first aspect of the present invention, these circuits are implemented in adiabatic clock-powered logic, and in accordance with the second aspect of the present invention self-timed logic circuits are employed that minimize reliance upon a clock signal to similarly minimize the clock tree.

It will also be understood that control and timing of IMD 100 can be accomplished with dedicated circuit hardware as described, for example, in the commonly assigned U.S. Pat. Nos. 5,391,188 and 5,292,342, or state machine logic rather than a programmed micro-computer. A state machine can advantageously be implemented in self-timed logic to perform state transitions asynchronously.

The IMD 100 also typically includes patient interface circuitry 104 for receiving signals from sensors or electrodes located at specific sites of a patient's body 10 and/or delivering a therapy to a site of the patient's body. The typical patient interface circuitry 104 therefore comprises a therapy delivery system 106 and/or a physiologic input signal processing circuit 108 or simply one or the other.

The physiologic input signal processing circuit 108 is coupled to electrodes and/or physiologic sensors on or in the housing of the IMD 100 or situated at sites distanced from the IMD housing, typically in distal portions of elongated leads. In the latter case, physiologic signals developed by such sensors or traversing the electrodes are coupled by way of elongated leads or catheters or transmitted through the body to physiologic input signal processing circuit 108. The physiologic input signal processing circuit 108 is formed of DSPs implemented either from adiabatic clock-powered logic or self-timed logic circuitry.

The IMD 100 can comprise an implantable cardiac monitor without a therapy delivery system 106, e.g., an implantable EGM monitor for recording the cardiac electrogram from electrodes remote from the heart as disclosed in commonly assigned U.S. Pat. No. 5,331,966 and PCT publication WO 98/02209. Or the IMD 100 can comprise an implantable hemodynamic monitor (IHM) for recording cardiac electrogram and other physiologic sensor derived signals, e.g., one or more of blood pressure, blood gases, temperature, electrical impedance of the heart and/or chest, and patient activity. The Medtronic® REVEAL® Insertable Loop Recorder having spaced housing EGM electrodes is an example of the former, and the Medtronic® CHRONICLE® IHM coupled with a capacitive pressure and temperature sensing lead and EGM sense electrodes of the type described in commonly assigned U.S. Pat. No. 5,564,434 is an example of the latter.

In these monitor embodiments, physiologic data, e.g., the cardiac EGM and/or sensor derived data is typically stored in RAM in microcomputer-based control and timing system 102 for uplink telemetry to an external programmer 110 when the IMD 100 receives a downlink telemetered interrogation command from the programmer 110. The data storage is either triggered by a timer of the IMD 100 on a periodic basis or by detection logic within the physiologic input signal processing circuit 108 upon satisfaction of certain event detection criteria. In some cases, the patient is provided with a magnet 116 or simplified external programmer 110 that can be applied over the subcutaneously implanted IMD 100 to trigger physiologic data storage when the patient experiences certain symptoms. In either case, event related data, e.g., the date and time, may be stored along with the stored episode data for uplink telemetry in a later interrogation session.

Therapy delivery IMDs 100 include the therapy delivery system 106 that can take a variety of forms and typically involve delivering electrical stimulation to body muscle groups, the heart, the brain, other organs, selected nerves, and the spinal column or the delivery of drugs into organs for therapeutic treatment or into the spinal column for pain relief. It will be understood that most of these therapy delivery IMDs also have a physiologic input signal processing circuit 108 that processes physiologic signals that are used to trigger or modulate therapy delivery and are stored as physiologic signal data for later retrieval as described above.

With respect to therapy delivery device configurations, the IMD 100 and therapy delivery system 106 may be configured to operate an implantable heart assist device or pump implanted in patients awaiting a heart transplant operation. In this case, derived relative blood pressure and/or temperature values may be used to modulate the action of the pump to maintain adequate cardiac output. The IMD 100 and therapy delivery system 106 may also be configured as a cardiomyostimulator to stimulate a muscle surgically wrapped about the heart in synchrony with cardiac depolarizations to increase cardiac output of a diseased heart.

The IMD 100 and therapy delivery system 106 may be configured to include a substance delivery apparatus or pump which is coupled to a suitable catheter extending to a site of the patient's body to deliver a substance, e.g., a therapeutic or diagnostic agent or drug, from a substance reservoir. For example, a drug to treat hypertension may be delivered to the patient's heart or vascular system, or an analgesic may be delivered to the spinal column to relieve intractable pain.

Or IMD 100 may be configured as a cardiac stimulator for sensing cardiac signals and delivering pacing pulses or cardioversion/defibrillation shocks to the heart through therapy delivery system 106. The IMD 100 may include any one or a combination of an anti-tachycardia pacer, anti-bradycardia pacer, cardioverter and/or defibrillator having suitable leads and electrodes extending to the patient's heart as part of the IMD therapy delivery system 106.

Similarly, the IMD 100 and therapy delivery system 106 may be configured with appropriate lead borne electrodes as a deep brain stimulator to control Parkinson's disease, or as a spinal column stimulator or nerve stimulator to control pain. The IMD and therapy delivery system 106 may be configured with appropriate electrodes and/or sensors to detect cardiac ischemia and provide compensatory autonomous nerve stimulation.

The IMD 100, therapy delivery system 106, and physiologic input signal processing circuit 108 may also be configured as a cochlear implant responding to sensor sound transducer inputs and providing stimulation to the cochlea.

These are merely exemplary configurations of IMD 100, therapy delivery system 106, and physiologic input signal processing circuit 108 for therapy delivery and/or monitoring. In all cases, the micro-computer-based control and timing system 102 governs all operating functions employing an appropriate, programmable operating algorithm. FIG. 2 also depicts other typical components common to an IMD 100 in any of these therapy delivery and/or monitoring configurations.

For example, most such IMDs have programmable operating modes and parameters that are stored in RAM in the microcomputer-based control and timing system 102. The operating modes and parameter values can be remotely programmed using the external programmer 110 to transmit commands and values in a downlink telemetry link 114 between external telemetry antenna 112 and IMD telemetry antenna 134 and received and decoded in the telemetry I/O circuit 124 in a manner well known in the art. The application of a magnetic field to a field responsive IMD switch 130, e.g., a reed switch or MAGFET, to provide a telemetry control signal RS from the reed switch circuit 120 is also typically required in current programming and interrogation protocols to enable communications between IMD 100 and external programmer 110. The above-referenced '188 and '342 patents disclose an alternative programming protocol that simply employs the magnet 116 and a MAGFET employed as the IMD switch 130 to make programming changes in a low cost pacing system architecture. Other telemetry protocols have been disclosed that operate at a greater distance between the antennae 112 and 134 and do not rely upon the magnetic field induced closure of the IMD switch 130.

All current IMDs rely upon a source of electrical energy to power the IMD operating system including the circuitry of IMD 100 and to power any electromechanical devices, e.g., valves, pumps, etc. of a substance delivery IMD or to provide electrical stimulation energy of an ICD shock generator, cardiac pacing pulse generator or other electrical stimulation generator. The typical energy source is a high energy density, low voltage battery 136 coupled with a power supply/POR circuit 126 having power-on-reset (POR) capability. The power supply/POR circuit 126 provides one or more low voltage power Vlo, the POR signal, one or more VREF power, current sources, an elective replacement indicator (ERI) signal, and, in the case of an ICD, high voltage power Vhi to the therapy delivery system 106. Not all of the conventional interconnections of these voltages and signals are shown in FIG. 2.

In addition, in certain IMDs, an audible patient alert warning or message is generated by a transducer 128 when driven by a patient alert driver 118 to advise of device operations, battery power level or a monitored patient condition. In ICDs, the patient may be warned of the detection of a malignant tachyarrhythmia and the imminent delivery of a cardioversion/defibrillationshock to enable the patient to assume a resting position prior to delivery.

Figure 1:
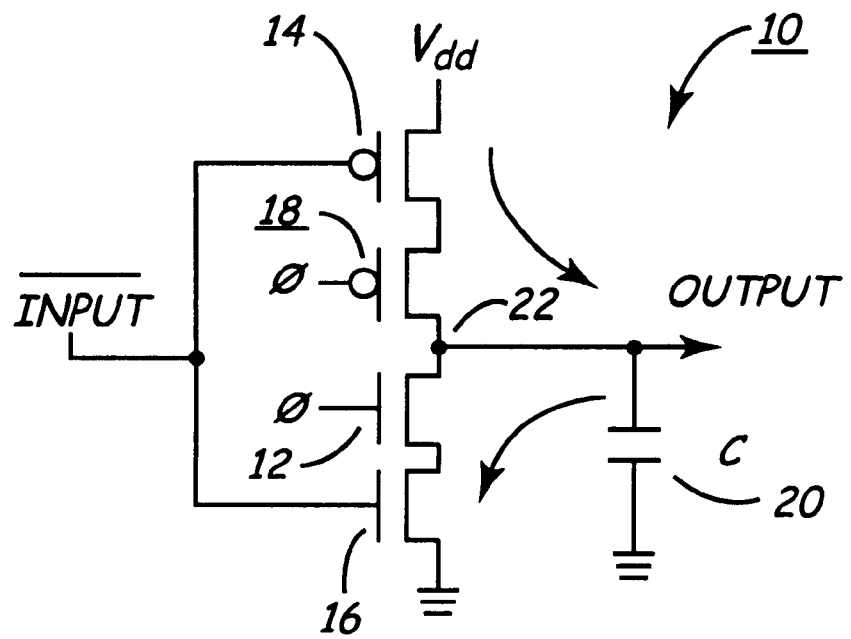
FIG. 1 is a circuit diagram illustrating prior art, clocked logic CMOS circuitry implementing an inverting function.

Virtually all current electronic IMDs are fabricated as described employing one or more clocked logic ICs that requires a clock signal CLK provided by a piezoelectric crystal 132 and system clock 122 coupled thereto to operate as shown in FIG. 1. In accordance with one aspect of the present invention, certain adiabatic clock signals, e.g., the ramped clock signals depicted in FIGS. 6A and 6B are developed by the clock circuits of FIGS. 5 and 7–10 within system clock 122 and routed to all applicable adiabatic clock-powered logic via a clock tree 138. Alternatively, the clock signals are developed locally at the distributed clock-powered logic. One or more CLK signal that is independent of the battery voltage over an operating battery voltage range is generated and distributed for system timing and control functions.

In FIG. 2, the clock tree 138 is shown in solid lines extending to the telemetry I/O block 124, the therapy delivery system 106, and the microcomputer-based control and timing system 102, where adiabatic clock-powered logic is employed at least to some extent in accordance with the present invention, and in broken lines to physiologic input signal processing circuit 108. In accordance with the first aspect of the present invention, adiabatic clock-powered logic is employed in the physiologic input signal processing circuit 108. But, the physiologic input signal processing circuit 108 may be implemented in self-timed logic in accordance with the second aspect of the present invention. Self-timed logic and other unclocked logic may be employed in other parts of therapy delivery system 106, the microcomputer-based control and timing system 102, and in certain downlink telemetry signal reception and decoding stages in the telemetry I/O circuit 124. FIG. 2 thus depicts a number of components of exemplary IMD system architectures in which the present invention may be implemented to lower current drain by use of adiabatic clock-powered logic alone or in combination with self-timed logic. It will be understood that other circuit blocks may be included in the exemplary IMD system.

Figure 3:
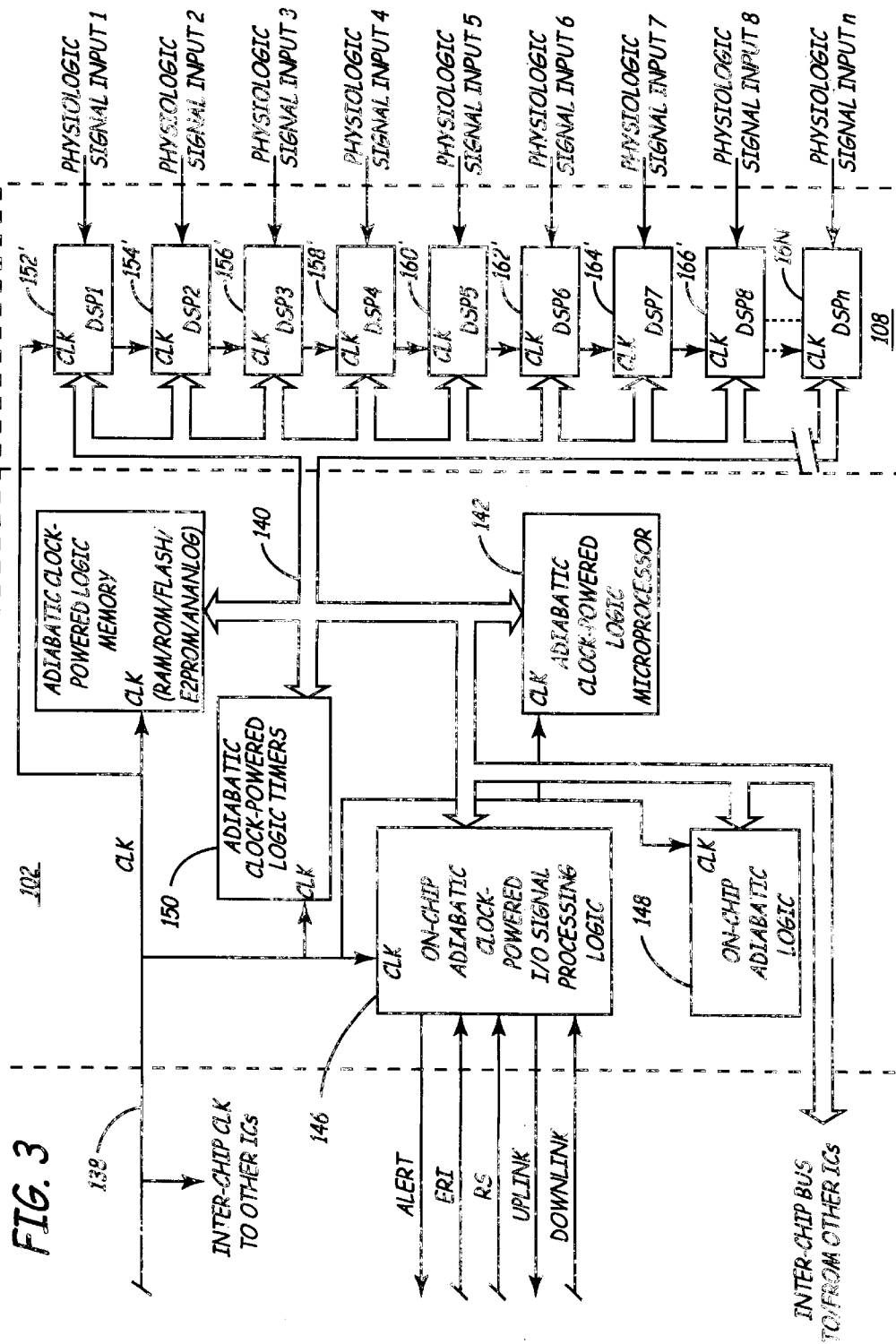
FIG. 3 is a detailed block diagram of the microcomputer-based control and timing system and physiologic input signal processing circuit of FIG. 2 for an exemplary IMD.

FIG. 3 depicts the microcomputer-based control and timing system 102 and physiologic input signal processing circuit 108 of FIG. 2 for an exemplary IMD 100 in greater detail, The microcomputer-based control and timing system 102 and physiologic input signal processing circuit 108 are formed on a single IC. The microcomputer-based control and timing system 102 comprises a microprocessor 142, memory circuit 144, on-chip I/O signal processing logic block 146, and on-chip logic block 148, all or portions of which may be implemented in adiabatic clock-powered logic or in self-timed logic, coupled together by a data and control bus 140. A set of adiabatic clock-powered logic timers 150 are also coupled with the other depicted components of the microcomputer-based control and timing system 102 by the data and control bus 140.

The data and control bus 140 also interconnects the components of microcomputer-based control and timing system 102 with DSPs 152–168 (also denoted DSP1–DSPn) of physiologic input signal processing circuit 108 and with any other ICs of the IMD 100. The data and control bus 140 may be formed of adiabatic CMOS logic circuitry to generate ramped and sinusoidal clock and data pulses as described in the above-referenced, co-pending '288 application. The DSPs 152–168, depicted in greater detail in FIG. 15, receive signals from the microcomputer-based control and timing system 102 on the data and control bus 140, process analog physiologic input signals, and provide digitized output signals on the data and control bus 140 to the components of the microcomputer-based control and timing system 102. The DSPs 152–168 are implemented either in adiabatic clock-powered logic or in self-timed logic.

The on-chip adiabatic clock-powered I/O signal logic block 146 generates the patient alert trigger signals delivered to the patient alert driver circuit 118 and processes the RS signal generated by reed switch circuit 120 and ERI signal generated by a battery voltage monitor circuit in power supply/POR circuit block 126. The on-chip adiabatic clock-powered I/O signal processing logic block 146 also provides timing control of data flow on data and control bus 140. The on-chip adiabatic clock-powered I/O signal processing logic block 146 also can include certain uplink and downlink telemetry signal processing stages. For example, the downlink telemetry signal may be processed by a DSP of the type depicted in FIG. 15 and described below located in on-chip adiabatic clock-powered I/O signal processing logic 146 to differentiate legitimate downlink telemetry signals from EMI and noise, e.g., signals emitted by theft detectors. Other inputs and outputs that are not time dependent, i.e., do not require timing out a time period, can be generated by adiabatic clock-powered I/O signal processing logic block 146. The on-chip, adiabatic clock-powered I/O signal processing logic block 146 may, however, be prompted to provide an output or process an input by an output of an adiabatic clock-powered logic timer 150.

The on-chip logic block 148 can include data management and computation circuits typically associated with the microprocessor based systems and data buses, including, for example, a direct memory address (DMA) controller, a block mover/reader, and a cyclic redundancy code (CRC) calculator. The on-chip logic block 148 may also include circuits that are prompted to provide an output or process an input by an output of an adiabatic clock-powered logic timer 150.

The adiabatic clock-powered logic timers 150 can time out time periods that are started by a trigger signal received from the on-chip logic blocks 146 and 148 or the DSPs 152–168. The adiabatic clock-powered logic timers 150 may also include a real time clock to append date and time stamp data to data stored in RAM in memory 144 or to trigger certain daily tests and operations, e.g. stimulation threshold tests, battery voltage tests and the like.

The IMD 100 of FIG. 2, incorporating the microcomputer-based timing and control system 102 and physiologic input signal processing circuit 108 of FIG. 3 can be configured to operate as a pacing system as described in detail below or as an ICD, brain stimulator or other nerve, organ or muscle stimulator, and is particularly useful where a multitude of sensors or sense electrode pairs are employed in the system. For example, multiple sensing and stimulation electrodes can be employed in bladder stimulation, deep brain stimulation or diaphragm stimulation. A comprehensive four chamber pacing system is described below with reference to FIG. 16.

Figure 4:
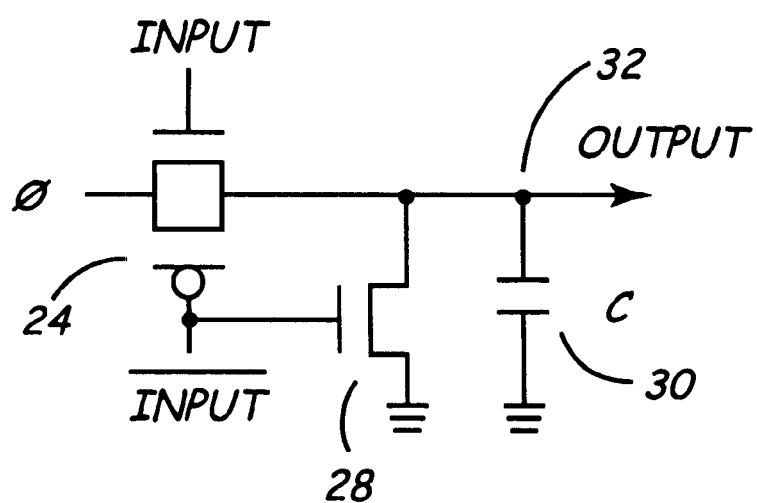
FIG. 4 is a circuit diagram illustrating clock-powered gate logic CMOS circuitry implementing an inverting function.

The form of adiabatic logic referred to herein as adiabatic clock-powered logic utilizes the energy of the clock pulse itself to charge the output node to the logic one HIGH level is exemplified by the buffer circuit depicted in FIG. 4. In clock-powered logic, large, on-chip, capacitive loads are charged and discharged directly by the clocks. The input, in dual rail form, controls a transmission gate (T-gate) 24 and a clamp FET 28. When the input is logic LOW, the output at node 32 is held LOW by the conduction of clamp FET 28. When the input is logic HIGH, the clock Ø passes through the T-gate 24 and charges the load represented by capacitor 30. Thus, supply voltage VDD is not employed to charge load capacitor 30 as is the case in the buffer depicted in FIG. 1 and described above.

Adiabatic logic circuits also strive to avoid the occurrence of a sudden and large potential difference across a switch when that switch is closed, and in this way limit power dissipation or recycle the charge. The power dissipated across a resistive device, such as a switch, is equal to $I^2R$, and it is possible to limit the energy dissipated by controlling the rate at which charge traverses the switch (i.e. controlling the current I). Accordingly, adiabatic circuits strive to:

(1) only close a switch when the potential difference across the switch is zero (or at least at a minimum); and (2) slowly increase, or ramp, a voltage source from which charge is transferred across the switch. It will be appreciated that the slower the rate of increase of the voltage, the slower the rate at which the charge will traverse the switch, and the less the energy dissipated.

Similarly, clock-powered logic circuits as depicted in FIG. 4 consume lower power when the path from the clock Ø to the output capacitor 30 charges adiabatically. When the load capacitor 30 is included in the path, the dissipated energy is approximated by the equation:

$$E_{diss}=(RC/T)CV^2.$$

Thus, less energy is dissipated if the clock transition time T (including rise time and fall time) is made longer than the RC time constant of path including the T-gate 24 and output capacitor 30.

The adiabatic clock-powered logic gate of FIG. 4 charges the capacitor 30 using the passed HIGH clock energy, if a change in state is dictated by the input signal, during the first half of the clock cycle. The changed or unchanged state (voltage on node 32) is read at the input of any the downstream clock-powered or other circuit that it is coupled with. The clamp transistor 16 holds the node 32 LOW if that is the state dictated by the input signal.

Thus, it is desirable to recover the energy on capacitor 30 if it is discharged at the end of the clock cycle. That energy can be recovered back through the T-gate 24 at the clock generator if ramped or sinusoidal clock voltage waveforms to effect energy recovery from the capacitor 30 are used.

Figure 5:
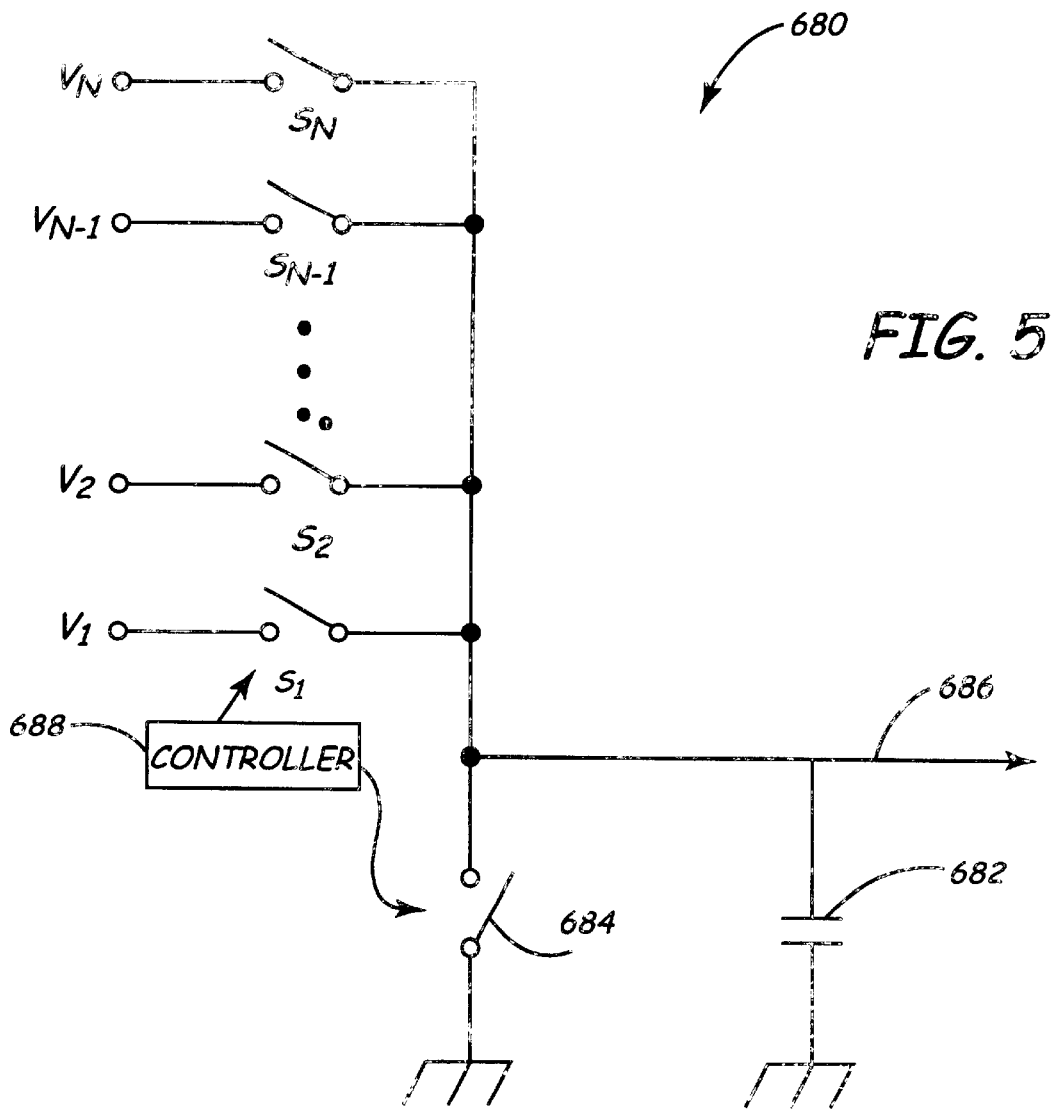
FIG. 5 is a circuit diagram illustrating one form of adiabatic clock waveform generating circuitry for use with the clock-powered gate logic CMOS circuitry of FIG. 4.
Figure 6A:
FIG. 6A and 6B graphically illustrates a ramped adiabatic clock waveform for use with the clock-powered gate logic CMOS circuitry of FIG. 4 and created by the adiabatic clock generating circuitry of FIGS. 5 and 7–9.
Figure 6B:

FIG. 5 is a circuit diagram illustrating one form of adiabatic clock waveform generating circuitry 680 for use with the adiabatic clock-powered gate logic CMOS circuitry of FIG. 4 to minimize power dissipation of clock energy during a switching operation. Circuitry 680 operates at a relatively low clock frequency, such as less than 500 kilohertz. As shown in FIG. 5, circuit 680 includes capacitor 682, switch 684, controller 688, switches $S_1-S_N$, and voltages $V_1-V_N$.

Controller 688 is a standard controller known in the art that controls the operation of switches $S_1-S_N$ and switch 684 by logic level changes. Circuitry 680 charges capacitor 682 through several intermediate steps to thereby produce ramped clock signal 686, which is transmitted to various sub-components of microcomputer-based timing and control system 102 and optionally physiologic input signal processing circuit 108. Ramped clock signal 686 is adiabatic in nature, which minimizes power dissipation thereby increasing the useful lifetime of the battery and IMD 100. A ramped clock signal 686 according to the invention is applied through the T-gate 24 of the adiabatic clock-powered logic circuitry of FIG. 4 to cause the node 32 receiving ramped clock signal 686 to gradually change states to thereby reduce dissipation energy of the interelectrode capacitance of the CMOS T-gate 24.

Supply voltages $V_1$–$V_N$ are used to charge capacitor 682. In one preferred embodiment, supply voltages $V_1$–$V_N$ are evenly distributed between ground and $V_N$ so that the voltage difference between any two adjacent supplies is the same. Each of the supply voltages is selectively applied to capacitor 682 by N switches including the first switch $S_1$ and N−1 additional switches. Switch 684 is closed to reset the voltage on capacitor 682 to an initial condition. To charge capacitor 682, switch 684 is opened and supply voltages $V_1$–$V_N$ are connected to capacitor 682 in succession by selectively closing and opening the switches $S_1$–$S_N$, that is, by momentarily closing switch $S_1$, opening switch $S_1$, momentarily closing switch $S_2$, etc., The supply voltages, $V_{N-1}$ through $V_1$ are switched in reverse order to discharge the load. Switch 684 is then closed, connecting the output node to ground.

If N steps are used, the dissipation energy per step is calculated using the following formula:

$$E_{step} = 1/C_L V^2$$

where $C_L$ is the capacitance at capacitor 682 and V is the supplied voltage. The dissipation energy is calculated in joules. Thus, N steps are used to charge capacitor 682 all the way to supply voltage V. A full charge-discharge cycle will result in twice the dissipation energy of the charging only. Thus, according to this analysis, charging by several steps reduces the dissipation energy per charge-discharge cycle, and thereby the total power dissipation, by a factor of N.

FIGS. 6A and 6B are graphs illustrating the adiabatic clock for use with the clock-powered gate logic CMOS circuitry of FIG. 4 and created by the adiabatic clock generating circuitry of FIGS. 5 and 7–9. FIG. 6A is a timing diagram illustrating voltage versus time at capacitor 682 shown in FIG. 5. As shown in FIG. 6A, the voltage at capacitor 682 is gradually ramped up from zero volts to supply voltage V. Similarly, the voltage is then ramped down from supply voltage V to zero volts. With the transition of ramped clock signal 686 from low to high and high to low in a gradual manner, minimal energy is released in the form of dissipated power during a switching operation.

Alternatively, circuit 680, shown in FIG. 5, produces a similar but different timing diagram from that shown in FIG. 6A. The timing diagram for this alternative scenario is shown in FIG. 6B. The capacitor 682 is charged from zero volts to supply voltage V in the same manner as previously discussed. However, in order to provide a discharge portion of the cycle, switch 684 is closed, which exponentially discharges the voltage at capacitor 682. It should be noted that this exemplary embodiment assumes a smaller, higher resistance switch 684 than the previous examples.

Figure 7:
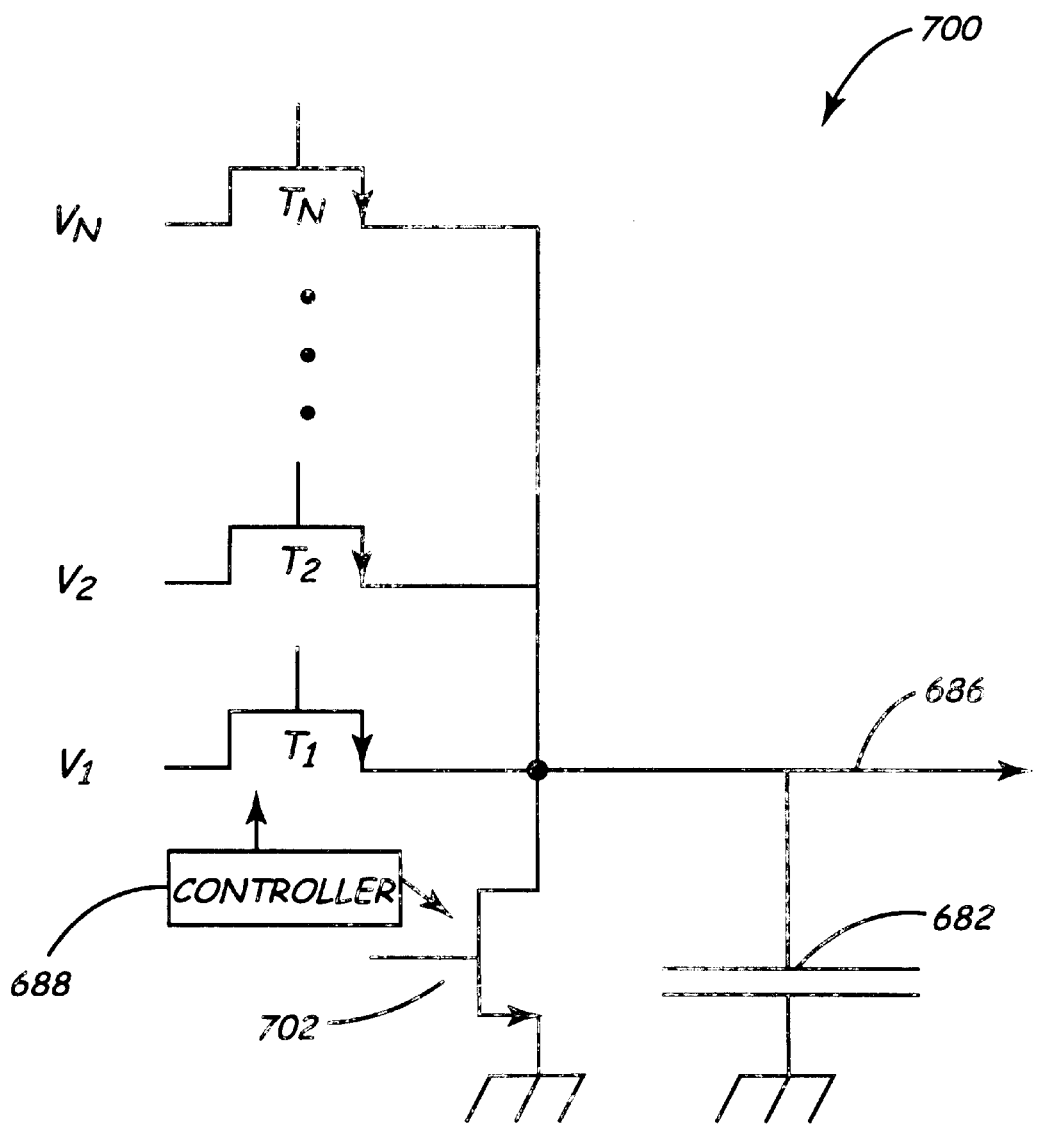
FIG. 7 is a circuit diagram illustrating a further form of adiabatic clock waveform generating circuitry for use with the clock-powered gate logic CMOS circuitry of FIG. 4.

FIG. 7 is a circuit diagram illustrating a further form of adiabatic clock waveform generating circuitry for use with the clock-powered gate logic CMOS circuitry of FIG. 4 and producing the clock signal illustrated in FIGS. 6A or 6B. Circuitry 700 is similar to and operates in a similar manner to circuitry 680 shown in FIG. 5, except that transistors $T_1$–$T_N$ replacing switches $S_1$–$S_N$. In one preferred embodiment, transistors $T_1$–$T_N$ are either N channel or P channel CMOS devices. Transistors $T_1$–$T_N$ and transistor 702 are turned on and off by controller 688 as in FIG. 5. Transistor 702 can be used to set an initial, known condition on capacitor 682. Transistor 702 is switched open and supply voltages $V_1$–$V_N$ are connected to capacitor 682 in succession to charge the capacitor 682 as described above with respect to FIG. 5. To discharge the capacitor 682, the supply voltages $V_1$–$V_N$ are applied to the load in reverse order, and transistor 702 is then closed, connecting the node 706 to ground to provide the clock waveform depicted in FIG. 6A. Alternatively, the exponential discharge waveform of FIG. 6B is produced if all of the transistors $T_1$–$T_N$ are simultaneously opened and transistor 702 is closed, thereby creating a resistive discharge path to ground for voltage on capacitor 682.

Figure 8:
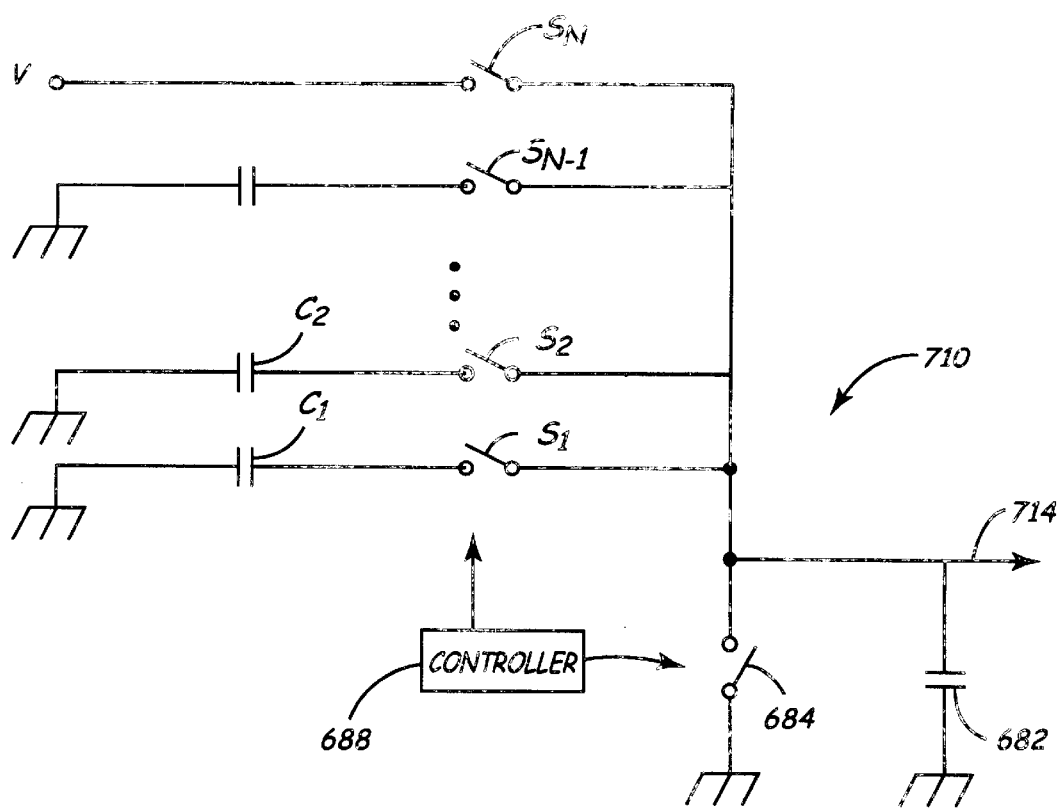
FIG. 8 is a circuit diagram illustrating a further form of adiabatic clock waveform generating circuitry for use with the clock-powered gate logic CMOS circuitry of FIG. 4.

FIG. 8 is a circuit diagram illustrating a further form of adiabatic clock waveform generating circuitry for use with the clock-powered gate logic CMOS circuitry of FIG. 4. Circuitry 710, is similar to circuitry 680 shown in FIG. 7, operating at a frequency of less than 500 kilohertz. However, capacitors $C_1$–$C_{N-1}$ replaces voltage sources $V_1$–$V_{N-1}$ connected between ground and switches $S_1$–$S_{N-1}$, respectively. In one preferred embodiment, capacitors $C_1$–$C_{N-1}$ are tank capacitors with a capacitance much larger (e.g., in order of magnitude) than capacitor 682. Once again, in one preferred embodiment, capacitor 682 represents an internal capacitance comprising the total capacitance of the internal nodes connected to a bus. In one preferred embodiment, capacitors $C_1$–$C_{N-1}$ have identical values to produce a symmetrical clock signal 714.

Figure 9:
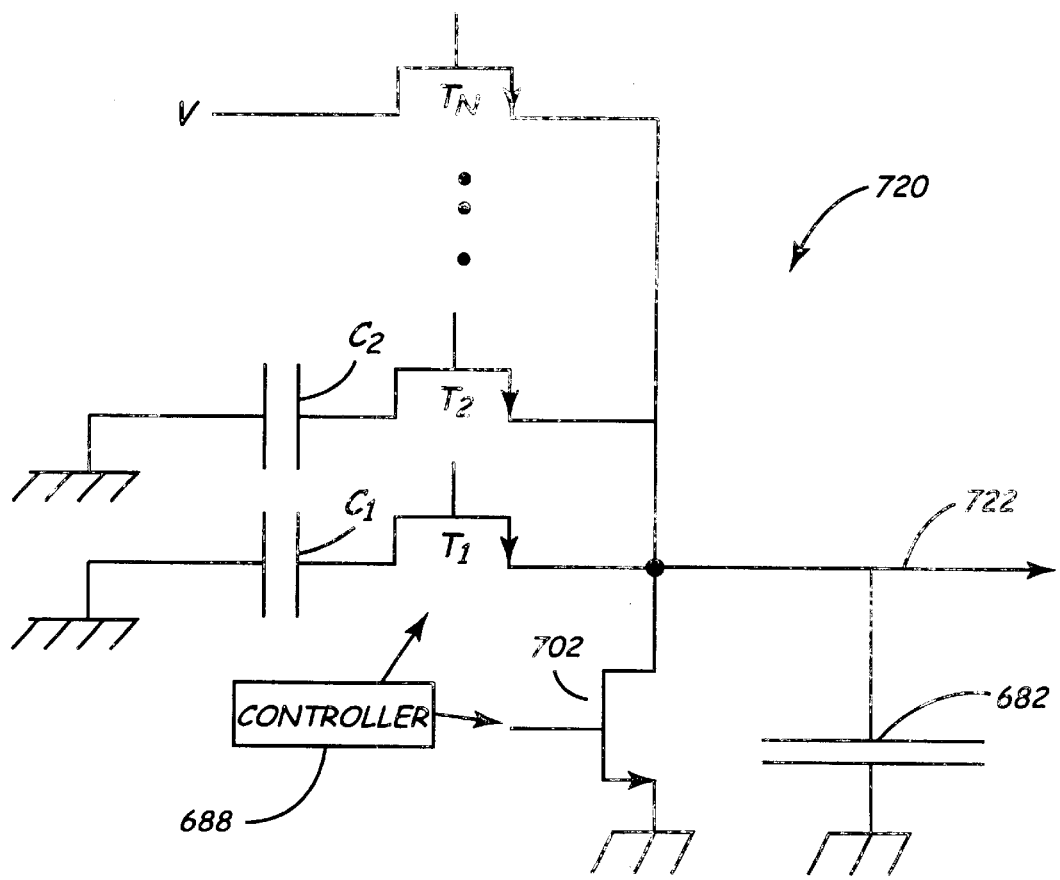
FIG. 9 is a circuit diagram illustrating a further form of adiabatic clock waveform generating circuitry for use with the clock-powered gate logic CMOS circuitry of FIG.4.

FIG. 9 is a circuit diagram illustrating a further form of adiabatic clock waveform generating circuitry for use with the clock-powered gate logic CMOS circuitry of FIG. 4. Circuitry 720 is similar to circuitry 710, shown in FIG. 8, with the exception that transistors $T_1$–$T_N$ replace switches $S_1$–$S_N$. As previously discussed, capacitors $C_1$–$C_{N-1}$ can be tank capacitors and transistors $T_1$–$T_N$ and 702 can be controlled by control 704. In one preferred embodiment, transistors $T_1$–$T_N$ can be either N channel or P channel devices. Circuitry 720 provides a ramped clock signal 722.

The embodiments shown in FIGS. 8 and 9 produce a similar logic signal to that shown in FIGS. 6A and 6B. Depending upon the operation of the circuitry, both circuits produce either a step-up and step-down ramp logic signal or produce a step-up and exponential down logic signal. In either case, the use of adiabatic logic reduces power dissipation during a switching operation.

Figure 10:
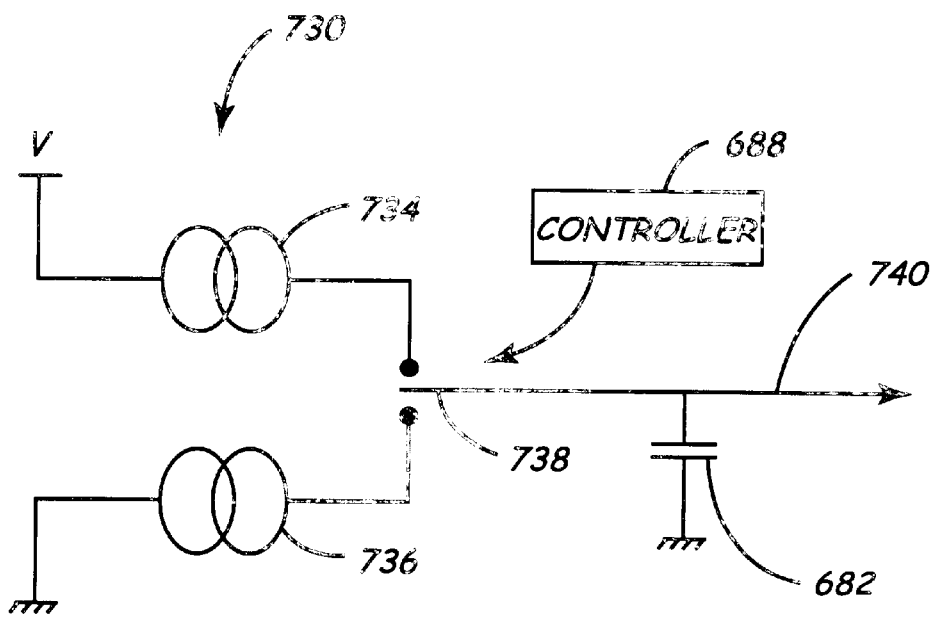
FIG. 10 is a circuit diagram illustrating a further form of adiabatic clock waveform generating circuitry for use with the clock-powered gate logic CMOS circuitry of FIG. 4.

FIG. 10 is a circuit diagram illustrating a further form of adiabatic clock waveform generating circuitry 730 that provides exponential waveform clock signal for use with the clock-powered gate logic CMOS circuitry of FIG. 4. Circuitry 730 includes voltage source V, current sources 734 and 736, and switch 738. Current source 734 is connected between voltage source V and switch 738, while current source 736 is connected between switch 738 and ground. The position of switch 738 determines whether capacitor 682 is charging or discharging. Due to the charging and discharging capabilities of capacitor 682, circuitry 730 will produce an exponential clock waveform 740 as shown in FIG. 11.

Figure 11:
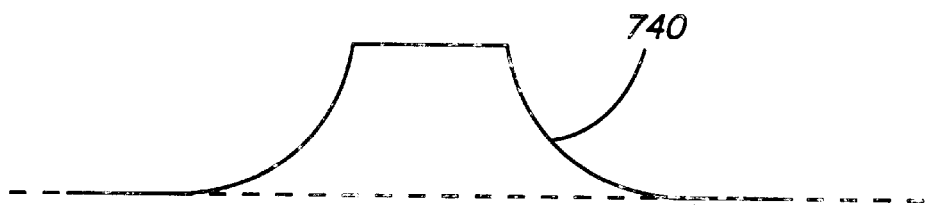
FIG. 11 graphically illustrates an exponential adiabatic clock waveform for use with the clock-powered gate logic CMOS circuitry of FIG. 4 and created by the adiabatic clock generating circuitry of FIG. 10.

As can be seen in FIG. 11, circuitry 730 produces an exponentially increasing first portion of exponential logic signal 740, while also producing an exponentially decreasing second portion of exponential logic signal 740. In one preferred embodiment, current source 734 and 736 would have identical values, such as in the range of 10–1000 pA.

The principles of operation of the adiabatic clock circuitry of FIGS. 5–11 are further described in U.S. Pat. Nos. 5,473,526 and in the above-referenced Svennson book chapter, for example.

Figure 12:
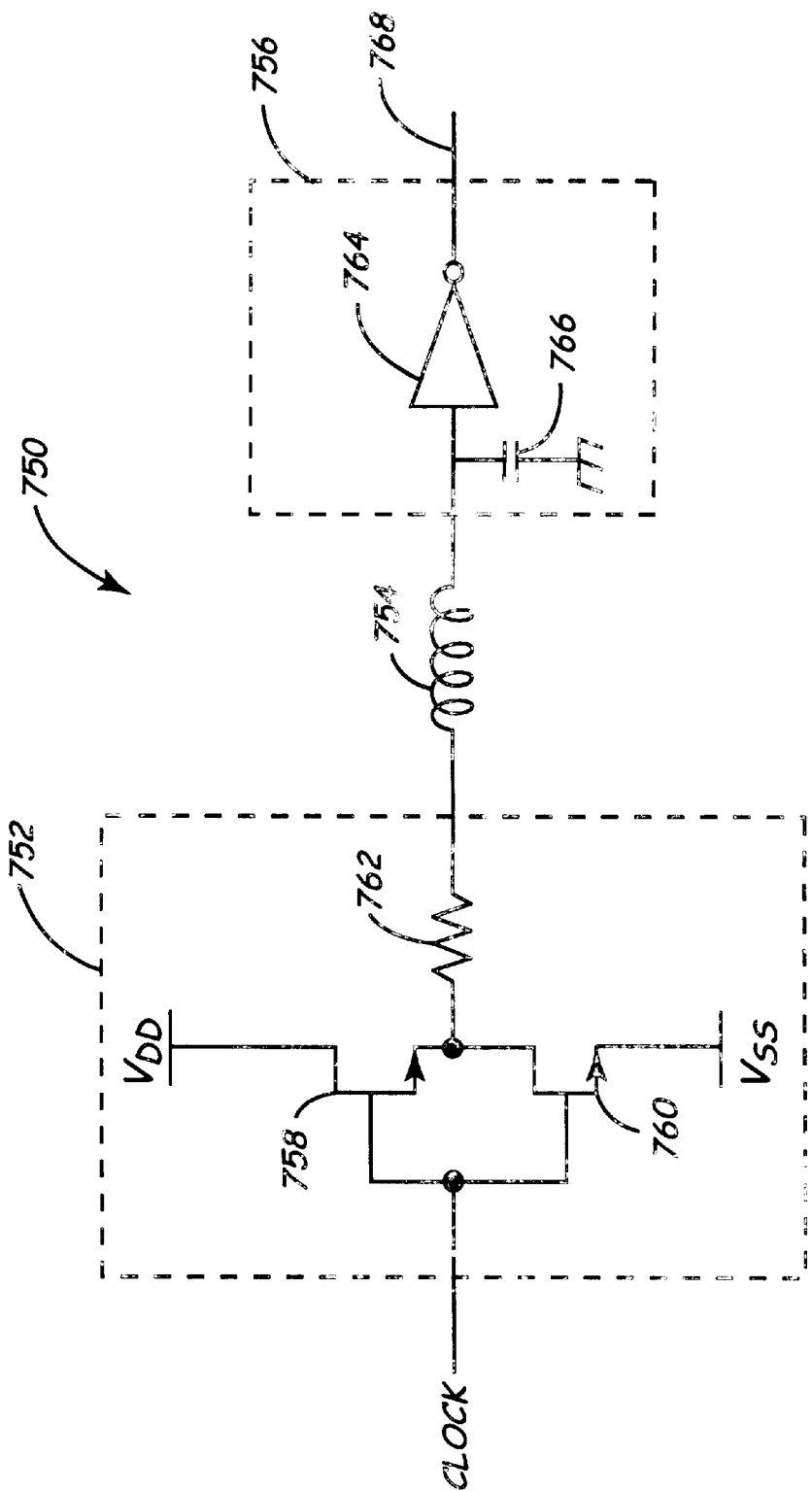
FIG. 12 is a circuit diagram illustrating a further form of adiabatic clock waveform generating circuitry for use with the clock-powered gate logic CMOS circuitry of FIG. 4.

FIG. 12 is a circuit diagram illustrating a further form of adiabatic clock waveform generating circuitry 750 for use with the clock-powered gate logic CMOS circuitry of FIG. 4 which minimizes power dissipation of the continuously switching clock signal. While the embodiment shown in FIGS. 5 and 7–11 are used in conjunction with a bus within IMD 100, circuitry 750 is used within IMD 100 in conjunction with a clock signal. For example, circuitry 750, shown in FIG. 12, can be used within system clocks 122 or in conjunction with microcomputer-based control and timing system 102 shown in FIG. 2. As shown in FIG. 12, circuitry 750 includes buffer circuit 752, inductor 754, and inverter circuit 756. Buffer circuit 752 further includes transistors 758 and 760, voltage sources VDD and VSS, and resistor 762, which represents an output resistance of buffer 752. Inverter circuit 756 further comprises inverter element 764 and capacitor 766, which represents an internal nodal input capacitance of inverter circuit 756.

The major components of circuitry 750 shown in FIG. 12 include inductor 754 in series with buffer circuit 752 and inverter circuit 756. Buffer circuit 752 includes transistors 758 and 760 set across voltage sources VDD and VSS. The transistors are in series with resistor 762, which is in turn serially connected to inductor 754. Similarly, inverter circuit 756 includes inverter element 764 connected in series with inductor 754. Capacitor 766 represents an internal capacitance between an input of inventor element 764 and ground.

Circuitry 750, shown in FIG. 12, utilizes one-half of the energy to power an equivalent logic circuit used in a standard clock signal compared to a prior art design. Buffer 752 via large P-type transistor 758 produces a fast rising edge of a standard square wave. The falling edge output of buffer 752 is produced by a much smaller N-type transistor 760. This pairing of large, P-type transistor 758 and small, N-type transistor 760 substantially decreases the crowbar current in buffer 752. The falling or trailing edge of logic signal 768 is produced by allowing circuitry 750 to simply ring with the negative cycle. Thus, circuitry 750 reduces the power consumption of a standard circuit by one-half, while enabling generation of logic signal 768 for transmission to a sub-component of IMD 100. The principles of circuitry 750 of FIG. 12 are further described in U.S. Pat. No. 5,559,478 and can be employed to provide two or more phase clock signals in the manner described in the '478 patent.

Figure 15:
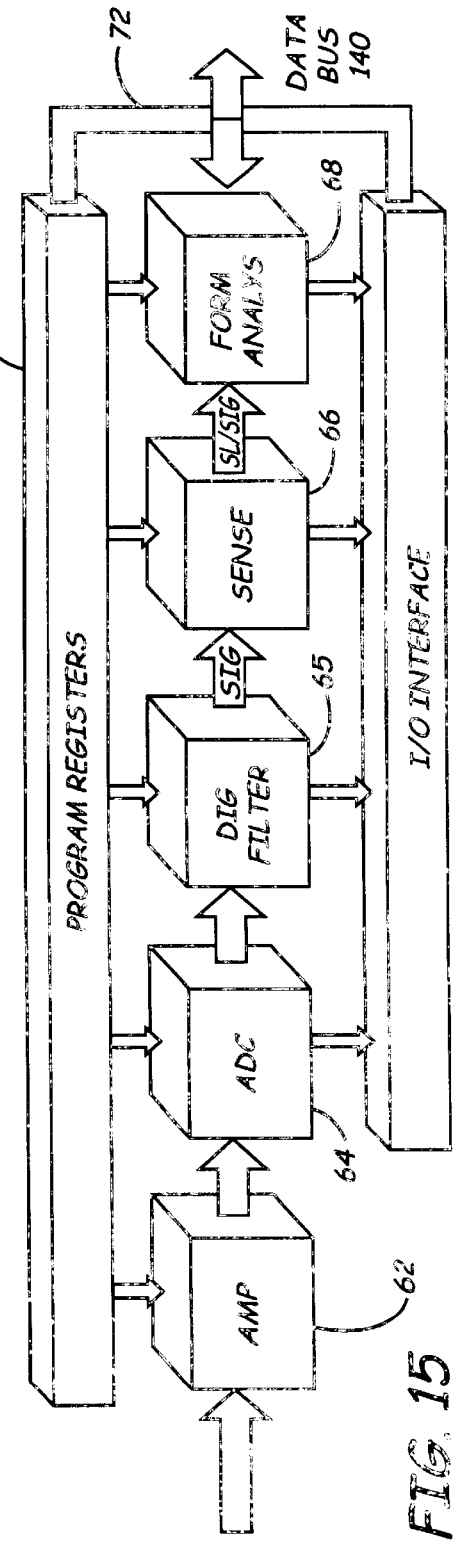
FIG. 15 is a detailed block diagram of a DSP embodied in self-timed logic elements or in adiabatic clock-powered logic employed for physiologic input signal processing.

In one embodiment of the invention, adiabatic clock-powered logic permits more functions to be performed by the DSPs shown in FIG. 15 due to the reduced power dissipation. Further, multiple processor based designs may also be implemented including adiabatic logic to reduce power dissipation as supply voltages and clocking frequencies are reduced for various functions performed by the processors.

While implementation of such adiabatic clock-powered logic in IMD operating systems as described above has advantages, it may be even more advantageous to selectively combine adiabatic clock-powered logic and self-timed logic in the same IMD operating system. Clocked logic circuits are affected by clock skew and race conditions which become more severe as the clock tree extends to ever increasing numbers of switched logic elements on a given IC or on separate ICs. A great deal of design time, effort, and expense must be expended in timing analysis, worst case timing simulations, etc., of a given IC layout to arrive at a final IC layout that minimizes these adverse conditions.

At least two self-timed logic schemes have been devised in recent years that differ from conventional clocked Boolean logic in a variety of ways. Fundamentally, self-timed logic elements, like clocked Boolean logic elements, have at least one and typically two or more inputs and an output and provide an output level that may or may not be changed when an input level changes pursuant to governing logic rules of the particular element and any other input signal levels. Clocked Boolean logic elements process the input level change in timed relation to a clock signal occurring after the input level change. Self-timed logic responds to and propagates an input level change without the delay attendant to awaiting a clock signal. The output level of a self-timed logic element changes after a self-propagation time, if change is dictated by the applicable rules and the other input levels. Thus, in a self-timed logic circuit formed of a plurality of self-timed logic elements, data flow propagates from the circuit input to the circuit output through the logic elements (sometimes referred to as nodes or cells) analogous to following a flow chart. The processing of a change in an input signal level or state takes as much time as is necessary, not one or more clock cycles, to sequentially traverse the chain of self-timed logic elements to the output and to resume a state of readiness to accept and process a succeeding change in an input signal level. Within such a self-timed logic circuit, the power consumption due to clock energy dissipation is obviously eliminated, and residual ground or substrate noise level is also reduced by the absence of the clock signal.

Figure 13:
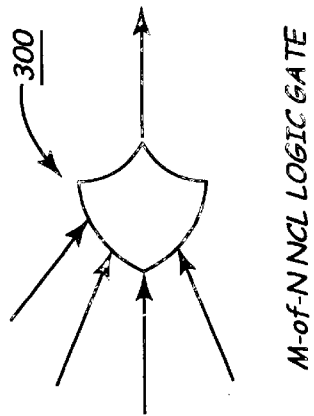
FIG. 13 is a schematic illustration of a first form of self-timed logic.

Delay insensitive data encoding, referred to as Null Convention Logic™ (NCL) has been developed by Theseus Logic Inc., Orlando, Fla., and described in a number of publications and in U.S. Pat. No. 5,350,463 and a subsequently issued series of related patents. The fundamental NCL cell or element 300 depicted in FIG. 13 features three logic states, True(1), False(0) and Null, and a feedback loop and is devised as an M-of-N threshold gate with hysteresis that processes a DATA(1) and DATA(2) input level. In CMOS implementation, DATA is represented by a "high" level, e.g., VDD and NULL is a "low" level or ground. The output of a fundamental NCL cell or element 300 is maintained at its current state through hysteresis, and a new output cannot be asserted until a complete set of DATA input levels are present at M-of-N inputs. When the output asserts DATA, it will not change to NULL until all N inputs are NULL. These characteristics of a circuit devised of NCL cells or elements are represented to define a symbolically complete logic which is self-timed and independent of the propagation delays of its component cells or elements at the logic level. Consequently, a circuit formed of fundamental NCL cells or elements does not experience "racing" or exhibit spurious outputs.

The mathematical expressions and theory of NCL and its implementation in two value logic for a variety of gates, flip-flops, and the like, are set forth by Fant et al. in "NULL Convention Logic™" (Theseus Logic, Inc., 1997, 35 pp.), by Wang et al. in "Technology Independent Design Using NULL Convention Logic™" (Theseus Logic, inc., Oct. 19, 1998 19 pp.), and in the above-referenced '463 patent and other patents assigned to Theseus Logic, Inc. The design and fabrication of NCL building blocks, e.g. DSPs, logic circuits, timers, and high speed micro-processor cores, have been announced by Theseus Logic, Inc. and partners including Sanders Associates, Motorola, Inc., and the Defense Advanced Research Projects Agency (DARPA) as reported at http://www.sanders.com/hpc/cl/overview.html.

Figure 14:
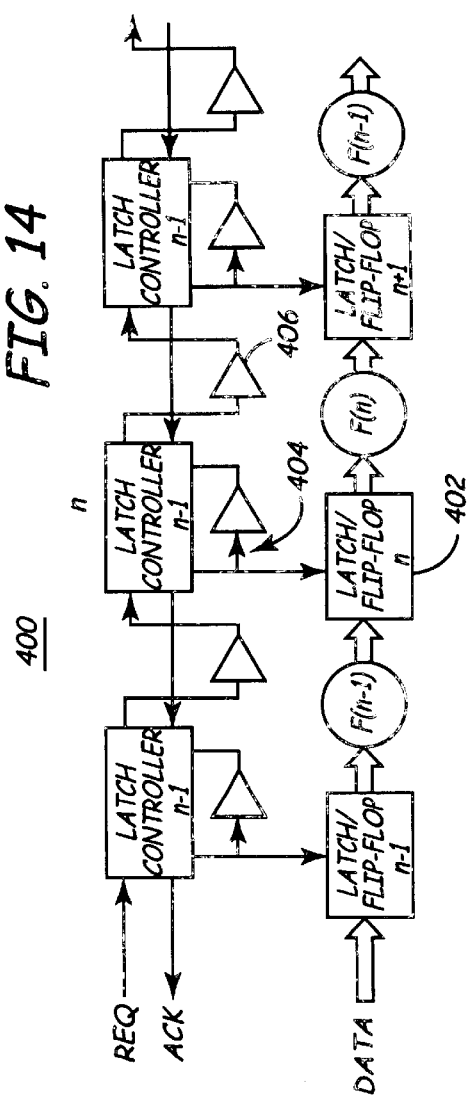
FIG. 14 is a schematic illustration of a second form of self-timed logic.

A self-timed control logic design 400 advanced by Cogency Technology, Inc., Toronto, Ontario, CANADA, and illustrated in FIG. 14 advances data through a self-timed circuit that comprises a sequence of data handling stages each stage, e.g., stage "n", comprising a flip-flop or latch 402 for storing a data level, a latch-controller 404, and a delay matching element 406. Incoming data from an upstream input source or a upstream stage is accompanied by a request (REQ) directed to the latch-controller of the receiving stage. The latch-controller of the receiving stage responds to the REQ with an acknowledgment (ACK) sent to the upstream latch-controller, and stores the incoming bundled DATA in the flip-flop or latch of the receiving stage. The delay matching element at the output of the latch of each stage simply delays the control signals long enough for the combinational logic functions on the data path to settle. The REQ, ACK, and DATA together are called a "channel", and the above described communication over a channel is called a "handshake". See "Introduction to Self-Timed Design" (Cogency Technology @ hftp//:www.cogency.co.uk/tech/index.html, © 1999, 8 pp.)

These publicized efforts are directed at development of self-timed logic microprocessors and circuit building blocks that operate at high speed comparable to 500 MHz or greater clock speeds and to reduce or eliminate the consumption of such high speed clock power and its dissipation as heat in relatively large scale computing systems. Such computational power and speed are not necessary for the IMD applications described above in reference to FIG. 2, and heat dissipation is not an issue in relatively low speed IMD data flow, computations and timing as described above.

However, the reduction in power caused by elimination of the clock is important for limiting energy consumption by the limited capacity, low voltage batteries employed in IMDs. And minimizing the clock tree frees up IC chip real estate to accommodate additional circuitry. Moreover, self-timed logic circuitry can operate reliably over a broader range of $V_{DD}$ and is less sensitive to IC process changes than clocked logic. Supply voltage lowers in IMDs as battery depletion occurs which can cause clocked logic circuits to become unreliable, whereas self-timed logic circuits simply slow incrementally as supply voltage decreases but operate well within timing constraints in which IMD functions have to be performed. IC process changes that affect the sequence of clocked logic operations and can cause clock timing conflicts are readily implemented in self-timed logic circuits.

FIG. 15 illustrates the principal blocks of a DSP IC 50 integrated with a first stage analog amplifier and filter 62 having a filter characteristic of about 0.7 to 500 Hz, for example. The DSP IC 50 includes an ADC 64 for performing A/D conversion, a digital filter block 65, a sense block 66 and a form analysis block 68 coupled to program registers 75 and I/O interface 70 and a local bus 72 coupled to data and control bus 140 of FIGS. 2 and 3. The general principles of operation of a DSP implemented in self-timed logic are disclosed, for example, in the article by Jacobs et al., entitled "A Fully Asynchronous Digital Signal Processor Using Self-Timed Circuits", *IEEE Journal of Solid-State Circuits*, vol. 25, no. 6, December 1990, pp. 1526–1536.

The DSP IC 50 can be alternatively implemented in adiabatic clock-powered logic circuitry coupled through a system clock tree to receive the adiabatic clock signals provided as described above from a system adiabatic clock generator or having a locally disposed adiabatic clock signal generator and a local clock tree. The general principles of operation of a DSP implemented in adiabatic clocked logic is disclosed, for example, in the paper by Athas et al. entitled "Energy Recovery CMOS for Highly Pipelined DSP Designs" (*IEEE Proc. Intl. Symp. on Low Power Electronics and Design*, Monterey, Calif., Aug. 12–14, 1996, 4 pp.). The DSP IC 50 that processes the physiologic signal comprises a plurality of adiabatic clock-powered logic elements formed into a chain that receives the physiologic signal at an input thereof, processes the physiologic signal and provides the processed physiologic signal at an output in timed relation to the adiabatic clock signal as described below.

The amplified and filtered analog input signal is processed by ADC 64 to generate a digital output signal at a predetermined sampling frequency, e.g., 256 or 512 samples per second for cardiac signals. The ADC 64 can be clocked at the selected sampling frequency by way of an on-board local oscillator or can be implemented in self-timed logic as disclosed, for example, in U.S. Pat. No. 5,014,057.

The DSP1–DSPn IC 50 depicted in FIG. 15 provides analog-to-digital conversion of the physiologic signal provided by said sensing means and signal processing of the digitized physiologic signals input thereto as shown in FIGS. 2 and 3 to provide processed output signals to bus 140. Specifically, the output signals of physiologic sensors of the types described above can be sampled, digitized and processed by DSP1 and DSP2 and the far field and near field EGM can be sampled, digitized and processed by DSP7 and DSP8 in FIG. 3. Moreover, the digitized physiologic input signals can be processed in DSP1–DSPn of FIG. 3 with reference to event detection criteria or other predetermined discrimination criteria for determining the presence or absence of a predefined characteristic of the physiologic signal and providing a sense event signal upon determination of the pre-defined characteristic. Specifically, the cardiac signals conducted from the sense electrode pairs coupled to the inputs of DSP3–DSP5 of FIG. 16 can be digitized, processed and compared to specified P-wave, R-wave and T-wave detection criteria appropriate to each electrode site to provide accurate sense event output signals in FIG. 16.

The ADC 64 is suitably a delta-sigma modulator followed by a decimeter to provide typically 8-bit bytes at the chosen sampling interval. The bytes that are outputted from ADC 64 are then applied to digital filter 65 which is suitably a digital bandpass filter having a characteristic to remove high frequency artifacts, low frequency signal components, and the offset of the ADC 64. The filtered byte signal SIG output from digital filter 65 are applied to sense block 66. Sense block 66 obtains the slew rate, or slope SL, of the digitized and digitally filtered signal SIG corresponding to an event that is to be classified. The slope signals SL are processed with the SIG signal by form analysis block 68. In the case of a sense amplifier function performed by DSP IC 50, form analysis block 68 provides a sense event output to bus 140 if and when sense event criteria are satisfied by the SIG and SL signals. The detailed description of the operation of the sense block 66 and form analysis block 68 appears in the above-referenced '318 application.

The signal processing characteristics of each ADC 64, digital filter 65, sense block 66, and form analysis block 68 of each DSP1–DSPn can be specifically tailored in program registers 75 to provide optimal event detection of a specific input signal characteristic or processing of the input signal for accuracy and fidelity. The sampled byte signal processing through these components downstream of ADC 64 proceeds at the propagation speed allowed by the self-timed logic element chain, and can be readily accomplished in the sample periods between each A/D conversion by ADC 64.

Figure 16:
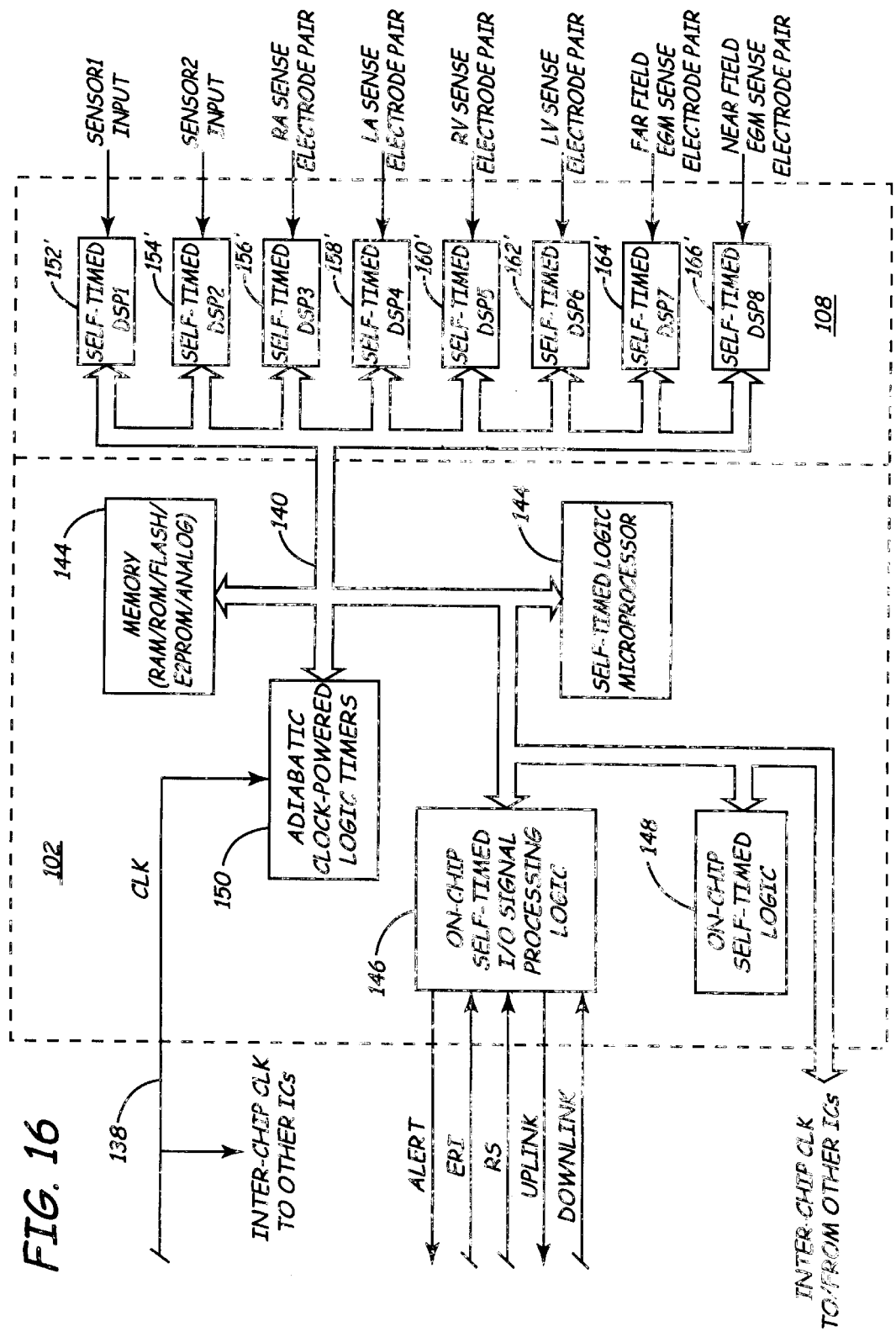
FIG. 16 is a detailed block diagram of the microcomputer-based control and timing system and physiologic input signal processing circuit of FIG. 3 for a multi-chamber pacing system that is preferably implemented employing a combination of self-timed logic elements or in adiabatic clock-powered logic.

FIG. 16 is a detailed block diagram of the microcomputer-based control and timing system and physiologic input signal processing circuit of FIG. 2 for a multi-chamber pacing system of the type described, for example, in commonly assigned U.S. Pat. No. 5,902,324 which can be implemented into a pacemaker IPG or into an ICD to provide pacing functions. In such multi-chamber pacing systems that have been disclosed in the prior art, pacing and sensing electrodes are distributed in relation to two, three or four heart chambers to provide pacing and sensing functions. Hybrid analog and digital sense amplifiers are coupled to selected electrode pairs for sensing characteristic cardiac signals of the PQRST electrogram originating in or traversing the heart chamber, and sense event signals are generated by the sense amplifiers when detection criteria tailored to the characteristic cardiac signals are satisfied. The sense event signals are treated as trigger or reset signals to start or terminate a timed period governed by the pacing operating algorithm. Complex operating algorithms for three and four chamber pacing systems are set forth in the above-referenced '324 patent and in commonly assigned, co-pending U.S. patent application Ser. No. 09/439,244 filed Nov. 12, 1999 for MULTI-SITE CARDIAC PACING SYSTEM HAVING CONDITIONAL REFRACTORY PERIOD.

In addition, further analog sense amplifiers are provided for providing EGM signals that are digitized by an ADC and then stored in RAM as episode data for uplink data transmission to the external programmer as described above is in reference to FIG. 2. Such conventional, prior art, sense amplifiers have become increasingly more complex as they are called upon to distinguish characteristics of interest in the cardiac signals in each of the heart chambers or in multi-site sensing in the same heart chamber. In a four chamber pacing system, separate sense amplifiers or a multi-plexed sense amplifier are coupled to each selected pair of sense electrodes distributed about the heart.

These problems and concerns can be alleviated through the selective use of self-timed logic and/or adiabatic clock-powered logic implemented DSPs in lieu of conventional analog and digital clocked logic circuits. FIG. 16 depicts a four chamber pacing system employing electrode pairs that would be selected for the right atrium (RA), left atrium (LA), right ventricle (RV) and left ventricle (LV) from which characteristic electrical signals of interest originating in or traversing each such chamber would be detected by such a DSP. Moreover, the near field or far field EGM would be sampled and processed by further DSPs coupled with selected bipolar or unipolar sense electrodes, respectively, for event or episode related EGM data storage. The DSPs performing EGM signal processing would have differing gain, filtering and signal processing characteristics than DSPs performing event detection, but some or all of the sense electrode pairs in the four chambers could be employed for both EGM signal processing and event detection. Thus, for example, the RA, LA, RV and LV sense electrode pairs are coupled to the inputs of self-timed logic DSP3, DSP4, DSP5 and DSP6, and selected pairs of far field and near field EGM sense electrodes are coupled to the inputs of self-timed logic DSP7 and DSP8.

In addition, the output signals of physiologic sensors are coupled to the inputs of self-timed logic DSP1 and DSP2. One or more physiologic sensor can be employed to derive signals reflecting the need for cardiac output experienced by a patient to adjust the pacing rate, and timing and sequence of delivery of pacing pulses to the right and left atria and ventricles. One such physiologic sensor may comprise an activity sensor mounted to the housing of the pacing system IPG, and another sensor may comprise a blood gas, blood pressure, temperature, minute ventilation (MV) or pH sensor. The output signals of such sensors are processed and combined in a pacing rate setting algorithm as disclosed, for example, in commonly assigned U.S. Pat. Nos. 5,282,839 and 5,562,711, for example, to derive an optimum pacing rate.

The substitution of clocked logic DSPs for such complex sense amplifiers and also for circuits that process output signals of physiologic sensors is set forth in commonly assigned, co-pending U.S. patent application Ser. No. 09/399,318 filed Sep. 20,1999, for CARDIAC PACING SYSTEM WITH IMPROVED PHYSIOLOGIC EVENT CLASSIFICATION AND HEART MONITORING BASED ON DSP and Ser. No. 09/181,460, filed Oct. 28, 1998, for POWER SUPPLY REDUCTION IN MEDICAL DEVICES USING MULTIPLE SUPPLY VOLTAGES AND CLOCK FREQUENCY CONTROL. The principles of operation of such DSPs remain the same whether they are implemented in adiabatic clock-powered logic or self-timed logic of the types described herein.

The microcomputer timing and control system 102 in FIG. 16 responds to cardiac sense event signals generated by DSP3–DSP7 in a variety of ways. Certain nonrefractory sense events terminate time-out of pacing escape intervals and delay intervals being timed out by adiabatic clock-powered logic timer block 150 as described further below. The timing and sequences of particular cardiac sense event signals are subjected to rate and pattern criteria to determine, for example, whether a tachyarrhythmia condition exists and to counter or ameliorate its effects by mode switching, rate stabilization, and the like. In addition, storage of the EGM signals output by DSP7 and DSP8 and physiologic sensor signals output by DSP1 and DSP2 in memory locations of RAM in memory 144 may be commenced. In this way, episode data may be stored for later retrieval and uplink telemetry to the external programmer 110.

The programmable escape interval is preferably timed out by an adiabatic clock-powered timer 150 that times out the programmed escape interval as multiples of the crystal oscillator generated clock interval. The adiabatic clock-powered logic microprocessor 142 responds to interrupts, e.g., a sense event signal or sensor output by a DSP, or time-out of the escape interval and other time periods, or receipt of a downlink telemetered signal or the like. The self-timed logic or adiabatic clock-powered logic microprocessor 142 performs the functions of controlling operating mode per the programmed-in operating mode and applies programmed operating parameter values, e.g., the programmed pacing escape interval, AV delay, and post-atrial and post-ventricular delays, at its own propagation speed upon receiving an interrupt and then returns to a dormant state.

The number n of DSP ICs 50 employed in the pacing system of FIG. 16 depends on how it is to be employed in a particular pacemaker IPG or ICD IPG. The multi-chamber pacing system depicted in FIG. 16 is particularly directed to pacing diseased hearts having conduction defects and/or in congestive heart failure (CHF). In CHF, cardiac depolarizations that naturally occur in one upper or lower heart chamber are not conducted in a timely fashion either within the heart chamber or to the other upper or lower heart chamber. In such cases, the right and left heart chambers do not contract in optimum synchrony with each other, and cardiac output suffers due to the conduction defects. In addition, spontaneous depolarizations of the left atrium or left ventricle occur at ectopic foci in these left heart chambers, and the natural activation sequence is grossly disturbed. In such cases, cardiac output deteriorates because the contractions of the right and left heart chambers are not synchronized sufficiently to eject blood therefrom. Furthermore, significant conduction disturbances between the right and left atria can result in left atrial flutter or fibrillation.

A number of proposals have been advanced for providing pacing therapies to alleviate these conditions and restore synchronous depolarization and contraction of a single heart chamber or right and left, upper and lower, heart chambers as described in detail in the above-referenced '324 patent and '244 patent application, for example.

It has been proposed that various conduction disturbances involving both bradycardia and tachycardia of a heart chamber could benefit from pacing pulses applied at multiple electrode sites positioned in or about a single heart chamber or in the right and left heart chambers in synchrony with a depolarization which has been sensed at least one of the electrode sites. It is believed that atrial and left ventricular cardiac output can be significantly improved when left and right chamber synchrony is restored through either simultaneous delivery or specified sequences of delivery of right and left heart chamber pacing pulses, particularly in patients suffering from dilated cardiomyopathy and CHF. In cases involving conduction defects of a single heart chamber, it is believed that an improvement in cardiac output can be achieved by locating pace/sense electrodes at specific sites of the single heart chamber and pacing all sites simultaneously or in particular order, depending upon the site where a sense event is first detected during time-out of a pacing escape interval.

In bi-chamber (bi-atrial or bi-ventricular) pacemakers, pacing pulses are delivered to one or the other or both of the right and left heart chambers upon expiration of a pacing escape interval. The escape interval is restarted upon delivery of a pacing pulse or upon a non-refractory right or left heart chamber sense event. Post-event time periods are started upon delivery of a pacing pulse or upon a refractory or non-refractory sense event. The delayed right-to-left or left-to-right conduction of an evoked depolarization resulting from delivery of a pacing pulse to the right or left heart chamber, respectively, and capture of that heart chamber traverses the non-paced pace/sense electrode after a delay that enables it to be sensed and mistakenly characterized as a refractory sense event. Here also, a second restarting of post-event time periods due to a mistakenly characterized refractory sense event can result in the failure to respond appropriately to the next true, spontaneous sense event in either of the right and left heart chambers. Thus, the timing of delivery of bi-atrial or bi-ventricular pacing pulses can also be disrupted.

Similar problems arise in AV sequential, bi-atrial and/or bi-ventricular pacing systems, wherein three or four heart chambers are paced and sensed. A V-A pacing escape interval is typically restarted by one of the following events: delivery of a ventricular pacing pulse at the time-out of an AV delay to one of the right or left or to both ventricles; a spontaneous, non-refractory, ventricular sense event sensed in one ventricle before the time-out of the AV delay; or a spontaneous, non-refractory, ventricular sense event sensed in one ventricle before the time-out of the V-A escape interval and typically after time-out of an upper rate interval (URI) that defines the maximum pacing rate. A set of post-ventricular event timers are started upon each such event and time out post-ventricular event periods, e.g. atrial and ventricular blanking periods and refractory periods and the URI. The post-ventricular event timers start a ventricular refractory period (VRP) and at least one post-ventricular event period that affects the treatment of an atrial sense event occurring during its time-out. For example, an atrial sense event occurring during the time-out of a post-ventricular atrial refractory period (PVARP) can be ignored for purposes of resetting the V-A escape interval and starting the AV delay. The PVARP is typically programmable and can be set to prevent any response to an atrial sense event that may be caused by sensing of the antegrade conduction of the spontaneous or evoked ventricular depolarization through the atria and to the atrial pace/sense electrodes. The PVARP, VRP and URI interval are restarted each time that a ventricular pacing pulse is delivered and whenever a refractory or non-refractory ventricular sense event occurs.

The V-A delay is also terminated by its time-out and delivery of the programmed atrial pace pulse or pulses or a non-refractory atrial sense event. An atrial refractory period (ARP) and an AV delay interval are commenced upon termination of the V-A escape interval. A single ventricular pace pulse or right and left ventricular pacing pulses are delivered at expiration of the AV delay interval or the AV delay interval is terminated by a non-refractory ventricular sense event detected before its time-out. The V-A escape interval is then restarted.

The delivery of pacing pulses to right and left heart atria and ventricles upon expiration of the AV delay and V-A escape interval, respectively, is governed by programmed sequence, which may be simultaneous or with a right-to-left or left-to-right delay and either be committed or inhibited by a sense event detected in the second chamber to be paced prior to time out of the delay. A similar operation is effected for multi-site pacing and sensing at spaced apart pace/sense electrode sites in a single atrial and/or ventricular heart chamber.

Problems surface in implementing multi-site pacing in a single heart chamber or in right and left heart chamber pacing within the contexts of conventional timing and control systems for characterizing and responding to sense event signals generated by sense amplifiers coupled to spaced apart pace/sense electrodes. Inappropriate responses can be triggered by depolarizations conducted between the separated pace/sense electrode sites and sensed by sense amplifiers coupled to those pace/sense electrodes which upset the timing of delivery of subsequent pacing pulses. In right and left heart pacing systems, pacing and sensing problems arise when right-to-left or left-to-right conduction delays vary depending on right and left ventricle pace/sense electrode placement, transient conditions of the heart, and chronic CHF.

The above-described pacing system of FIG. 16 can be tailored as such a bi-chamber pacing system for two, three or four chambers or as a multi-site single chamber pacing system wherein the DSPs that are utilized are tuned to accurately distinguish true refractory and non-refractory sense events and spontaneous and conducted sense events at each electrode site in a single heart chamber or the right and left heart chambers.

Although the preferred embodiment of a pacing system in which the present invention is described above is relatively complex, it will be understood that the same allocation of adiabatic clocked and self-timed logic can be provided in less complex pacing systems. Atrial or ventricular single chamber pacing system that typically functions in an AAI or AAIR mode or VVI or VVIR mode, respectively, or a conventional AV sequential pacing system functioning in the DDD or DDDR mode can be implemented with adiabatic clock-powered logic alone or with a combination of adiabatic clock-powered logic and self-timed logic.

The fabrication of adiabatic clock-powered logic alone or with self-timed logic in a single IC in the IMD operating system architectures of the present invention is compatible with various fabrication technologies such as silicon on insulator (SOI), silicon on sapphire (SOS) CMOS technologies as well as conventional silicon CMOS technologies. The present invention as described herein is enabling technology for the use of DSPs to perform more functions due to the manner in which power consumption can be reduced for such DSPs.

In addition, as the power consumption is reduced by incorporating adiabatic clock-powered logic of the invention into devices, further functionality can be added to the devices, thus taking advantage of the power conservation aspects of the present invention. For example, morphology detection functions may be added without increasing energy dissipation if the DSPs are implemented in clock-powered logic or self-timed logic. Specifically, differentiation of retrograde P-waves and antegrade P-waves of EGM waveform; differentiation of P-waves from far field R-waves; differentiation of AF-A flutter-AT from sinus tachycardia; differentiation of VT-VF-V flutter from SVT; and differentiation of cardiac signals from electromagnetic interference may be implemented using the detection circuits of the present invention.

While the present invention has been illustrated and described with particularity in terms of a preferred embodiment, it should be understood that no limitation of the scope of the invention is intended thereby. The scope of the invention is defined only by the claims appended hereto. It should also be understood that variations of the particular embodiment described herein incorporating the principles of the present invention will occur to those of ordinary skill in the art and yet be within the scope of the appended claims.

What is claimed is:

1. An implantable medical device for at least one of delivering a therapy to a patient's body and monitoring a physiologic condition of a patient comprising:

a battery providing battery energy; and at least one integrated circuit comprising an operating system, powered by the battery energy, providing control and timing functions and further comprising:

a clock circuit powered by the battery energy providing adiabatic clock signals;

a clock tree routing the adiabatic clock signals;

at least one adiabatic clock-powered logic circuit formed on said at least one integrated circuit coupled with said clock tree and responsive to said adiabatic clock signals to perform a defined circuit function employing the energy of the adiabatic clock signal and in timed synchrony with the adiabatic clock signal; and at least one self-timed logic circuit formed on said integrated circuit performing defined circuit functions independent of said adiabatic clock signals and not in timed synchrony with the adiabatic clock signals, whereby a clock tree is minimized and clock energy is conserved.

2. The implantable medical device of claim 1, further comprising:

means for sensing a physiologic condition of the patient and providing a physiologic signal; and wherein:

said self-timed logic circuit further comprises a signal processor processing the physiologic signal, the signal processor comprising a plurality of self-timed logic elements formed into a chain, the chain receiving the physiologic signal at an input thereof, processing the physiologic signal, and providing the processed physiologic signal at an output after a self-timed logic propagation delay, and wherein said plurality of self-timed logic elements perform functions independent of and not in timed synchrony with said adiabatic clock signals.

3. The implantable medical device of claim 2, wherein the signal processor comprises a digital signal processor providing analog-to-digital conversion of the physiologic signal provided by said sensing means and signal processing of a digitized physiologic signal.

4. The implantable medical device of claim 2, wherein the signal processor comprises a digital signal processor providing analog-to-digital conversion of the physiologic signal provided by said sensing means and processing a digitized physiologic signal with reference to predetermined discrimination criteria, determining the presence or absence of a predefined characteristic of the physiologic signal, and providing a sense event signal upon determination of the predefined characteristic.

5. The implantable medical device of claim 4, wherein:

said adiabatic clock-powered logic circuit comprises at least one timer timing out time periods as multiples of the clock time period in response to a sense event signal; and further comprising:

means responsive to time-out of a time period by said timer for performing a first device operation; and means responsive to a sense event signal provided during time-out of a time period for performing a second device operation.

6. The implantable medical device of claim 1, wherein said self-timed logic further comprises:

a microcomputer comprising a microprocessor, a timing and control bus, and RAM/ROM memory storing data and operating instruction sets of device operation algorithms that operates pursuant to the stored data and operating instruction sets to establish timed out time periods and performing at least one of therapy delivery and monitoring functions.

7. The implantable medical device of claim 6, further comprising:

means for sensing a physiologic condition of the patient and providing a physiologic signal; and wherein:

said self-timed logic circuit further comprises a signal processor processing the physiologic signal, said signal processor comprising a plurality of self-timed logic elements formed into a chain, the chain receiving the physiologic signal at an input thereof, processing the physiologic signal, and providing the processed physiologic signal at an output to said data and control bus after a self-timed logic propagation delay, and wherein said plurality of self-timed logic elements perform functions independent of and not in timed synchrony with said adiabatic clock signals.

8. The implantable medical device of claim 1, wherein said self-timed logic further comprises a plurality of self-timed logic elements formed into a chain receiving an input signal at an input thereof, processing the input signal and providing a processed output signal at an output thereof after a self-timed logic propagation delay, wherein said plurality of self-timed logic elements perform functions independent of and not in timed synchrony with said adiabatic clock signals.

9. An implantable medical device for at least one of delivering a therapy to a patient's body and monitoring a physiologic condition of a patient, comprising:

a battery providing battery energy;

means for sensing a physiologic condition of the patient and providing a physiologic signal; and at least one integrated circuit comprising an operating systems powered, by the battery energy, providing control and timing functions and further comprising:

a clock circuit powered by the battery energy providing adiabatic clock signals;

a clock tree routing the adiabatic clock signals; and at least one adiabatic clock-powered logic circuit formed on said integrated circuit coupled with said clock tree and responsive to said adiabatic clock signals to perform a defined circuit function employing the energy of the adiabatic clock signal and in timed synchrony with the adiabatic clock signal, said adiabatic clock-powered logic circuit further comprising a signal processor coupled to receive said adiabatic clock signals, said signal processor processing the physiologic signal and comprising a plurality of adiabatic clock-powered logic elements formed into a chain, the chain receiving the physiologic signal at an input thereof, processing the physiologic signal and providing the processed physiologic signal at an output in timed relation to the adiabatic clock signal, wherein said adiabatic clock-powered logic circuit further comprises a plurality of self-timed logic elements formed into a chain, the chain receiving an input signal at an input thereof, processing the input signal and providing a processed output signal at an output thereof in timed relation to the adiabatic clock signal, and wherein said plurality of self-timed logic elements perform functions independent of and not in timed synchrony with said adiabatic clock signals.

10. The implantable medical device of claim 9, wherein the signal processor further comprises a digital signal processor providing analog-to-digital conversion of the physiologic signal provided by said sensing means and signal processing of the digitized physiologic signal.

11. The implantable medical device of claim 10, wherein the signal processor further comprises a digital signal processor providing analog-to-digital conversion of the physiologic signal provided by said sensing means and processing the digitized physiologic signal with reference to predetermined discrimination criteria, determining the presence or absence of a predefined characteristic of the physiologic signal, and providing a sense event signal upon determination of the pre-defined characteristic.

12. The implantable medical device of claim 11, further comprising:

means for sensing a sense event of the patient; and wherein:

said adiabatic clock-powered logic circuit further comprises at least one timer timing out time periods as multiples of the clock time period; and further comprising:

means responsive to time-out of a time period by said timer for performing a first device operation; and means responsive to a sense event signal provided during time-out of a time period for performing a second device operation.

13. The implantable medical device of claim 9, wherein said adiabatic clock-powered logic circuit further comprises:

a microcomputer comprising a microprocessor, a timing and control bus, and RAM/ROM memory storing data and operating instruction sets of device operation algorithms operating pursuant to the stored data and operating instruction sets to establish timed out time periods and performing at least one of therapy delivery and monitoring functions.

14. The implantable medical device of claim 13, further comprising:

means for sensing a physiologic condition of the patient and providing a physiologic signal; and wherein:

said adiabatic logic circuit further comprises a signal processor coupled to said adiabatic clock and processing the physiologic signal, said signal processor comprising a plurality of logic elements formed into a chain, the chain receiving the physiologic signal at an input thereof, processing the physiologic signal and providing the processed physiologic signal at an output in timed relation to the adiabatic clock signal.

15. An implantable cardiac pacing system for sensing cardiac signals and delivering pacing pulses through pace/sense electrodes situated in one or more heart chamber comprising:

a battery providing battery energy; and at least one integrated circuit comprising an operating system, powered by the battery energy, providing control and pacing timing functions and further comprising:

an adiabatic clock signal generator powered by the battery energy and providing adiabatic clock signals;

an adiabatic clock-powered logic circuit formed on said integrated circuit and responsive to said adiabatic clock signals to time-out a pacing escape interval;

a clock tree formed on the integrated circuit coupling said adiabatic clock signals to the adiabatic clock-powered circuit; and at least one self-timed logic circuit formed on said integrated circuit performing defined circuit functions independent of said adiabatic clock signals and not in timed synchrony with the adiabatic clock signals, whereby the clock tree is minimized and clock energy is conserved; and means responsive to time-out of the pacing escape interval for generating and delivering a pacing pulse to the pace/sense electrodes.

16. The implantable pacing system of claim 15, wherein:

said self-timed logic circuit further comprises a signal processor coupled with said pace/sense electrodes processing the cardiac signal, said signal processor comprising a plurality of self-timed logic elements formed into a chain, the chain receiving the cardiac signal at an input thereof, processing the cardiac signal, and providing the processed cardiac signal at an output after a self-timed logic propagation delay, and wherein said plurality of self-timed logic elements perform functions independent of and not in timed synchrony with said adiabatic clock signals.

17. The implantable pacing system of claim 16, wherein the signal processor comprises a digital signal processor providing analog-to-digital conversion of the cardiac signal and processing the digitized physiologic signal.

18. The implantable pacing system of claim 17, wherein the signal processor comprises a digital signal processor providing analog-to-digital conversion of the cardiac signal, processing the digitized cardiac signal with reference to predetermined discrimination criteria, determining the presence or absence of a predefined characteristic of the cardiac signal, and providing a sense event signal upon determination of the pre-defined characteristic.

19. The implantable pacing system of claim 18, further comprising:

means for restarting the time-out of the pacing escape interval in response to a sense event signal.

20. The implantable pacing system of claim 15, wherein said self-timed logic further comprises:

a memory having a plurality of memory locations; and means for triggering storage of said processed cardiac signal in the plurality of memory locations.

21. The implantable pacing system of claim 15, wherein said self-timed logic further comprises a microcomputer comprising a microprocessor, a timing and control bus, and RAM/ROM memory storing data and operating instruction sets of device operation algorithms, the microcomputer operating pursuant to the stored data and operating instruction sets to establish timed out time periods and perform pacing pulse delivery and to adjust sensing criteria for sensing cardiac events.

22. The implantable pacing system of claim 11, further comprising:
    means for sensing a physiologic condition of the patient and providing a physiologic signal; and wherein:
        said self-timed logic circuit further comprises a signal processor processing the physiologic signal, said signal processor comprising a plurality of self-timed logic elements formed into a chain, the chain receiving the physiologic signal at an input thereof, processing the physiologic signal, and providing the processed physiologic signal at an output to said data and control bus after a self-timed logic propagation delay, and wherein said plurality of self-timed logic elements perform functions independent of and not in timed synchrony with said adiabatic clock signals.

23. An implantable medical monitor for periodically monitoring a physiologic condition of a patient comprising:
    physiologic sensor means for developing a physiologic sense signal;
    a battery providing battery energy;
    at least one integrated circuit formed of self-timed logic circuits comprising an operating system providing control and timing functions and further comprising:
        an adiabatic clock signal generator powered by the battery energy and providing adiabatic clock signals; and
        an adiabatic clock-powered logic circuit formed on said integrated circuit and responsive to said adiabatic clock signals to time-out a monitoring interval and generate a trigger signal upon time-out of the monitoring interval;
    means responsive to said trigger signal for triggering said physiologic sensor means to develop a physiologic sense signal; and
    a self-timed logic circuit formed on said integrated circuit performing defined circuit functions independent of and not in timed synchrony with said adiabatic clock signals.

24. The implantable medical monitor of claim 23 further comprising a memory having memory locations storing the processed physiologic sense signal data, and wherein said physiologic sensor means further comprises:
    a signal processor processing the physiologic sense signal each time the monitoring trigger signal is timed out, said signal processor comprising a plurality of self-timed logic elements formed into a chain, the chain receiving the physiologic signal at an input thereof, processing the physiologic signal, and providing the processed physiologic signal at an output after a self-timed logic propagation delay; and means for triggering storage of the processed physiologic sense signal data in said memory locations.

25. The implantable monitor of claim 23, wherein the physiologic sensor means comprises sense electrodes sensing an electrical signal of a body organ or muscle.

26. The implantable monitor of claim 23, wherein the physiologic sensor means comprises sense electrodes sensing a cardiac signal.

27. The implantable monitor of claim 23, wherein the physiologic sensor means comprises a physiologic sensor sensing a condition or state of the body from among the group consisting of physical activity of the body, blood pressure, blood temperature, blood gas concentration, and blood pH.

28. An implantable medical device powered by a battery for delivering a therapy on a timed basis to a patient dependent upon a physiologic condition of a patient comprising:
    physiologic sensor means for developing a physiologic sense signal;
    a signal processor processing the physiologic sense signal, said signal processor comprising a plurality of self-timed logic elements formed into a chain, the chain receiving the physiologic signal at an input thereof, processing the physiologic signal, and providing the processed physiologic signal at an output after a self-timed logic propagation delay;
    therapy delivery means for delivering a therapy to the patient in response to a therapy trigger signal;
    a battery providing battery energy; and
    at least one integrated circuit comprising an operating system receiving the processed physiologic signal and generating the therapy trigger signal, and further comprising:
        an adiabatic clock signal generator powered by the battery energy and providing adiabatic clock signals; and
        an adiabatic clock-powered logic circuit formed on said integrated circuit and responsive to said adiabatic clock signals to time-out a therapy delivery interval and generate a therapy trigger signal upon time-out of the therapy delivery interval, wherein said plurality of self-timed logic elements perform functions independent of and not in timed synchrony with said adiabatic clock signals.

29. The implantable medical device of claim 28, wherein the physiologic sensor means comprises sense electrodes sensing an electrical signal of a body organ or muscle.

30. The implantable monitor of claim 28, wherein the physiologic sensor means comprises sense electrodes sensing a cardiac signal.

31. The implantable monitor of claim 28, wherein the physiologic sensor means comprises a physiologic sensor sensing a condition or state of the body from among the group consisting of physical activity of the body, blood pressure, blood temperature, blood gas concentration, and blood pH.

* * * * *